(12) United States Patent
Takezawa et al.

(10) Patent No.: US 11,198,264 B2
(45) Date of Patent: Dec. 14, 2021

(54) DRIED HYDROGEL, DRIED VITRIGEL MEMBRANE, AND METHODS FOR PRODUCING THE SAME

(71) Applicants: NATIONAL INSTITUTE OF AGROBIOLOGICAL SCIENCES, Ibaraki (JP); Toshiaki Takezawa, Tokyo (JP); KANTO KAGAKU KABUSHIKI KAISHA, Tokyo (JP)

(72) Inventors: Toshiaki Takezawa, Tokyo (JP); Ayumi Oshikata, Ibaraki (JP); Hiroyuki Kuroyama, Kanagawa (JP); Tomoya Sawaguchi, Kanagawa (JP); Hiroyuki Yamaguchi, Kanagawa (JP)

(73) Assignees: KANTO KAGAKU KABUSHIKI KAISHA, Tokyo (JP); Toshiaki Takezawa, Tokyo (JP)

(*) Notice: Subject to any disclaimer, the term of this patent is extended or adjusted under 35 U.S.C. 154(b) by 426 days.

(21) Appl. No.: 14/326,817

(22) Filed: Jul. 9, 2014

(65) Prior Publication Data

US 2014/0319728 A1  Oct. 30, 2014

Related U.S. Application Data

(62) Division of application No. 13/818,759, filed as application No. PCT/JP2011/069191 on Aug. 25, 2011, now abandoned.

(30) Foreign Application Priority Data

Aug. 25, 2010  (JP) .............................. JP2010-188887

(51) Int. Cl.
  *C12M 3/00* (2006.01)
  *B29D 7/01* (2006.01)
  (Continued)

(52) U.S. Cl.
  CPC ................ *B29D 7/01* (2013.01); *B29C 39/02* (2013.01); *B29C 41/02* (2013.01); *C12N 5/0062* (2013.01); *B29K 2089/00* (2013.01); *C12M 25/14* (2013.01)

(58) Field of Classification Search
  CPC ........... B29D 7/01; B29C 41/02; B29C 39/02; C12N 5/0062; C12M 25/14; B29K 2089/00
  See application file for complete search history.

(56) References Cited

U.S. PATENT DOCUMENTS

| 7,195,912 B2 | 3/2007 | Takezawa et al. |
| 7,432,069 B2 | 10/2008 | Barman et al. |
| 2005/0129720 A1* | 6/2005 | Takezawa ............. A61L 31/005 424/400 |

FOREIGN PATENT DOCUMENTS

| JP | 2004155202 | * | 6/2004 |
| JP | 2007204881 | * | 8/2007 |

OTHER PUBLICATIONS

Takezawa, "Collagen Vitrigel: A Novel Scaffold that can faciliate a three-dimensional culture for reconstructing organoids." Cell Transplantation, vol. 13, pp. 463-473, 2004.*

(Continued)

*Primary Examiner* — Marcia S Noble
*Assistant Examiner* — Lauren K Van Buren
(74) *Attorney, Agent, or Firm* — Wenderoth, Lind & Ponack, L.L.P.

(57) ABSTRACT

A dried vitrigel membrane is produced by a method including the following steps of (1) a step of keeping a hydrogel in the inside of a wall surface mold with a shape the same as the desired shape disposed on a substrate, and discharging a part of free water within the hydrogel from a gap between the substrate and the wall surface mold; (2) a step of removing the wall surface mold from the top of the sub- (Continued)

strate; (3) a step of drying the hydrogel to remove the residual free water, thereby fabricating a vitrified dried hydrogel; (4) a step of rehydrating the dried hydrogel to fabricate a vitrigel membrane; and (5) a step of redrying the vitrigel membrane to remove free water, thereby fabricating a vitrified dried vitrigel membrane.

5 Claims, 16 Drawing Sheets

(51) Int. Cl.
    *B29C 39/02*     (2006.01)
    *B29C 41/02*     (2006.01)
    *C12N 5/00*     (2006.01)
    *C12M 1/12*     (2006.01)

(56) References Cited

OTHER PUBLICATIONS

Oorschot et al. "A Novel Flat-embedding Method to Prepare Ultrathin Cryosections from Cultured Cells in their in situ Orientaiton" The Journal of Histochemistry and Cytochemistry vol. 50(8): 1067-1080.*

Takezawa "Collagen Vitrigel: A Novel Scaffold that can facilitate a three-dimensional culture for reconstructing organoids." Cell Transplantation, vol. 13, pp. 463-373, 2004. (Year: 2004).*

Oorschot et al. "A Novel Flat-embedding Method to Prepare Ultrathin Cryosections from Cultured Cells in their in situ Orientaiton" The Journal of Histochemistry and Cytochemistry vol. 50(8): 1067-1080 (Year: 2002).*

T. Takezawa et al., "Collagen Vitrigel: A Novel Scaffold That Can Facilitate a Three-Dimensional Culture for Reconstructing Organoids", Cell Transplantation, vol. 13, pp. 463-473, 2004.

T. Takezawa et al., "A Protein-Permeable Scaffold of a Collagen Vitrigel Membrane Useful for Reconstructing Crosstalk Models between Two Different Cell Types", Cells Tissues Organs, vol. 185, pp. 237-241, 2007.

T. Takezawa et al., "Collagen vitrigel membrane useful for paracrine assays in vitro and drug delivery systems in vivo", Journal of Biotechnology, vol. 131, pp. 76-83, 2007.

Vernon et al. "Microgrooved fibrillar collagen membranes as scaffolds for cell support and alignment" Biomaterials 26 (2005) 3131-3140.

Takezawa et al. "A Protein-Permeable Scaffold of a Collagen Vitrigel Membrane Useful for Reconstructing Crosstalk Models between Two Different Cell Types" Cells Tissues Organs 2007; 185: 237-241.

Takezawa et al. "Collagen vitrigel membrane useful for paracrine assays in vitro and drug delivery systems in vivo" Journal of Biotechnology 131 (2007) 76-83.

Takezawa et al. "Collagen vitrigel: A Novel Scaffold that can facillitate a three-dimensional culture for reconstructing organoids" Cell Transplantation, vol. 13, p. 463-473, 2004.

\* cited by examiner

US 11,198,264 B2

DRIED HYDROGEL, DRIED VITRIGEL MEMBRANE, AND METHODS FOR PRODUCING THE SAME

TECHNICAL FIELD

The present invention relates to a dried hydrogel not having an amorphous outer peripheral edge, a dried vitrigel membrane, and methods for producing the same.

BACKGROUND ART

For studies of drug design, the development of culture systems capable of simply constructing three-dimensional culture models reflecting living bodies using various functional cells has been long demanded. In particular, a three-dimensional culture technology using a collagen gel for a cell culture carrier is useful for reconstructing a neovascularization model, a cancer infiltration model, an epithelial-mesenchymal model, and the like; however, it has not been widely spread yet.

As for the reasons therefor, it has been considered that since the conventional collagen gel is constituted of low-density fibers, it is so soft that its handling is difficult; since the conventional collagen gel is opaque, the phase-contrast microscopic observation of cultured cells is not always easy; and the like.

In order to solve these problems, the present inventor already established a technology for converting physical properties of a collagen gel into a thin membrane having excellent strength and transparency with good reproducibility, by injecting a sol of collagen to which optimum salt concentration and hydrogen ion concentration (pH) for gelation have been given into a Petri dish at a low temperature and further keeping the temperature at an optimum temperature to gelatinize the sol of collagen, followed by thoroughly drying at a low temperature, thereby gradually removing not only free water but bound water to achieve vitrification and subsequently rehydration (Patent Document 1).

Then, so far as a gel of other component than collagen is a hydrogel, by undergoing vitrification and then rehydration, it is possible to convert the gel into a novel stable state of physical properties, and therefore, the gel in a novel state of physical properties as fabricated through this vitrification step is named a vitrigel (Non-Patent Document 1).

In particular, thin collagen vitrigel membranes which have hitherto been developed are a transparent thin membrane having a thickness of several tens of micrometers, in which collagen fibers having a high density comparable to connective tissues in living bodies are entangled with each other and are characterized by having excellent protein permeability and strength. In addition, since various substances can be added to the collagen sol in the fabrication step, it is possible to reflect characteristics of the added substance on the thin collagen vitrigel membrane. Furthermore, for example, a thin collagen vitrigel membrane having a ring-shaped nylon membrane support imbedded therein can be easily handled by tweezers.

Then, the present inventor also proposed a technology in which this technology regarding thin collagen vitrigel membranes is more developed, thereby enhancing the transparency and fabrication reproducibility of thin collagen vitrigel membranes (Patent Document 2); a technology for fabricating a collagen vitrigel in not a membrane shape but a filamentous or tubular shape (Patent Document 3); and the like.

CITATION LIST

Patent Documents

Patent Document 1: JP-A-8-228768
Patent Document 2: WO 2005/014774
Patent Document 3: JP-A-2007-204881

Non-Patent Documents

Non-Patent Document 1: Takezawa T, et al., Cell Transplant. 13: 463-473, 2004
Non-Patent Document 2: Takezawa T, et al., Cells Tissues Organs 185: 237-241, 2007
Non-Patent Document 3: Takezawa T, et al., J. Biotechnol. 131: 76-83, 2007

SUMMARY OF THE INVENTION

Problem to be Solved by the Invention

However, in the conventional production method of a thin collagen vitrigel membrane, for example, as illustrated in FIG. 3, the thin collagen vitrigel membrane was produced by injecting a prescribed amount of a collagen sol into a plastic-made culture Petri dish to undergo gelation so as to have an arbitrary thickness, followed by vitrification by means of drying and rehydration.

For this reason, the dried collagen gel which had been vitrified by means of drying could be fabricated only in a state where it attached to the bottom surface and wall surface of the culture Petri dish. Therefore, there was encountered such a problem that the thin collagen vitrigel membrane originating in the wall surface was entrained at the time of rehydration. In the case where the thin collagen vitrigel membrane originating in the wall surface is entrained, handling of the thin collagen vitrigel membrane is difficult. Thus, in order to utilize the thin collagen vitrigel membrane as a three-dimensional culture carrier of cells, an operation for removing the unnecessary thin collagen vitrigel membrane portion originating in the wall surface is necessary. However, since the thin collagen vitrigel membrane contains moisture, this cutting work operation was not easy. In addition, by altering the shape of the container into which the collagen sol is injected, it was possible to control the shape of the formed thin collagen vitrigel membrane to some extent. However, since the thin collagen vitrigel membrane originating in the wall surface is entrained, in order to precisely work a fine shape, the moisture-containing thin collagen vitrigel membrane must be subjected to cutting work, and such was not easy. Then, in order to quickly mass-produce a thin collagen vitrigel membrane having an arbitrary shape as a product, it was an important problem to overcome such a complicated operation. In particular, with respect to the thin collagen vitrigel membrane having a ring-shaped nylon membrane support imbedded therein, which is utilized as a three-dimensional culture carrier of cells, it was necessary to finely work it in a shape in which the thin collagen vitrigel membrane attaches to only the bottom surface of the culture container and can be easily released from the bottom surface of the culture container by tweezers or the like as the need arises, namely a shape in which the thin collagen vitrigel membrane does not excessively protrude into the outer periphery of the ring-shaped nylon membrane support.

In addition, in the conventional production method of a thin collagen vitrigel membrane, since the removal of free water within the gel, which is a first step of vitrification, was conducted by means of natural drying by air-drying, in general, it took two or more days.

Then, according to the technologies up to date, with respect to control of the collagen content and thickness of the thin collagen vitrigel membrane, it was possible to fabricate a thin collagen vitrigel membrane containing collagen in an amount of from 100 μg to 1.0 mg per unit area (1.0 cm$^2$) by injecting a 0.25% collagen sol in an amount of from 0.04 to 0.4 mL per unit area (1.0 cm$^2$) of a culture Petri dish to undergo gelation, followed by vitrification and rehydration, and furthermore, it was possible to prepare the thin collagen vitrigel membrane in a thickness of from above several μm to several hundreds μm by adjusting the period of vitrification. For example, in the case of injecting a 0.25% collagen sol in an amount of 0.2 mL per unit area (1.0 cm$^2$) of a culture Petri dish to undergo gelation and then undergoing vitrification for two weeks or more, followed by rehydration, it was possible to fabricate a thin collagen vitrigel membrane in a thickness of about 15 μm; and in the case of similarly injecting 0.4 mL of a 0.25% collagen sol to undergo gelation and then undergoing vitrification for one week, followed by rehydration, it was possible to fabricate a thin collagen vitrigel membrane in a thickness of about 120 μm (Non-Patent Document 2).

However, in order to prepare a collagen vitrigel membrane which is not in a form of thin membrane but for example, has a thickness of 1 mm or more, it was considered that it is necessary to inject a 0.25% collagen sol in an amount of at least 3.3 mL or more per unit area (1.0 cm$^2$). But, so far as this amount is concerned, the collagen sol flows over existing Petri dishes, and hence, a special container must be prepared. Furthermore, after the gelation, in order to naturally dry free water within the gel, it takes ten or more days. For this reason, in order to quickly mass-produce a collagen vitrigel membrane, it was an important problem to shorten the time for removing a large quantity of free water within the gel.

Furthermore, according to the conventional production method, it is impossible to release a dried thin collagen vitrigel membrane from the culture Petri dish. Thus, the dried thin collagen vitrigel membrane was fabricated in a state where it attached to the bottom surface and wall surface of the culture Petri dish. For this reason, the dried thin collagen vitrigel membrane could not be freely handled in a state of membrane. Accordingly, it was also impossible to cut the dried thin collagen vitrigel membrane in an arbitrary fine shape.

Under the foregoing circumstances, the present invention has been made, and an object thereof is to provide a dried vitrigel membrane having a desired shape and having excellent characteristics such as practicality, handling properties, etc. and a dried hydrogel that is in a preliminary stage to this dried vitrigel membrane, and also methods for quickly mass-producing these dried vitrigel membrane and dried hydrogel.

Means for Solving the Problem

In order to solve the foregoing problem, the present invention provides the following dried vitrigel membrane, dried hydrogel, and methods for producing the same.

<1> A dried vitrigel membrane, characterized by not having an amorphous outer peripheral edge.
<2> The dried vitrigel membrane as set forth above in <1>, characterized by attaching to a substrate.
<3> The dried vitrigel membrane as set forth above in <1>, characterized in that the dried vitrigel membrane is superposed with a film possessing a capacity facilitating the detachability of the dried vitrigel membrane.
<4> The dried vitrigel membrane as set forth above in <3>, characterized in that the film is Parafilm.
<5> A dried hydrogel, characterized by not having an amorphous outer peripheral edge.
<6> The dried hydrogel as set forth above in <5>, characterized by attaching to a substrate.
<7> The dried hydrogel as set forth above in <5>, characterized in that the dried hydrogel is superposed with a film possessing a capacity facilitating the detachability of the dried hydrogel.
<8> The dried hydrogel as set forth above in <7>, characterized in that the film is Parafilm.
<9> A method for producing a dried vitrigel membrane having a desired shape, characterized by including the following steps of:
  (1) a step of keeping a hydrogel in the inside of a wall surface mold with a shape the same as the desired shape disposed on a substrate, and discharging a part of a free water within the hydrogel from a gap between the substrate and the wall surface mold;
  (2) a step of removing the wall surface mold from the top of the substrate;
  (3) a step of drying the hydrogel to remove the residual free water, thereby fabricating a vitrified dried hydrogel;
  (4) a step of rehydrating the dried hydrogel to fabricate a vitrigel membrane; and
  (5) a step of redrying the vitrigel membrane to remove free water, thereby fabricating a vitrified dried vitrigel membrane.
<10> The method for producing a dried vitrigel membrane as set forth above in <9>, characterized in that in the step (1), a support is introduced into the hydrogel in the inside of the wall surface mold.
<11> The method for producing a dried vitrigel membrane as set forth above in <9>, characterized in that in the step (1), the amount of the free water within the hydrogel is reduced to from about ¼ to ¾.
<12> The method for producing a dried vitrigel membrane as set forth above in <9>, characterized in that in the step (5), the dried vitrigel membrane is vitrified on a film possessing a capacity facilitating the detachability of the dried vitrigel membrane.
<13> The method for producing a dried vitrigel membrane as set forth above in <12>, characterized in that the film is Parafilm.
<14> A method for producing a dried vitrigel membrane capable of being molded in a desired shape, characterized by including the following steps of:
  (1) a step of keeping a hydrogel in the inside of a surface wall mold having an arbitrary shape, as disposed on a substrate on which a film possessing a capacity facilitating the detachability of the dried vitrigel membrane is laid, and discharging a part of free water within the hydrogel from a gap between the film on the substrate and the wall surface mold;
  (2) a step of removing the wall surface mold from the top of the substrate;
  (3) a step of drying the hydrogel to remove the residual free water, thereby fabricating a vitrified dried hydrogel;

(4) a step of rehydrating the dried hydrogel to fabricate a vitrigel membrane; and (5) a step of redrying the vitrigel membrane to remove free water, thereby fabricating a vitrified dried vitrigel membrane.

<15> The method for producing a dried vitrigel membrane as set forth above in <14>, characterized by after the step (5), including (6) a step of cutting the dried vitrigel membrane superposed with the film in a desired shape.

<16> The method for producing a dried vitrigel membrane as set forth above in <15>, characterized by after the step (6), including a step of releasing the dried vitrigel membrane from the film.

<17> The method for producing a dried vitrigel membrane as set forth above in <14>, characterized in that the film is Parafilm.

<18> The method for producing a dried vitrigel membrane as set forth above in <14>, characterized in that in the step (1), a support is introduced into the hydrogel in the inside of the wall surface mold.

<19> The method for producing a dried vitrigel membrane as set forth above in <14>, characterized in that in the step (1), the amount of the free water within the hydrogel is reduced to from about ¼ to ¾.

<20> A method for producing a dried hydrogel having a desired shape, characterized by including the following steps of:

(1) a step of keeping a hydrogel in the inside of a wall surface mold with a shape the same as the desired shape disposed on a substrate, and discharging a part of a free water within the hydrogel from a gap between the substrate and the wall surface mold;

(2) a step of removing the wall surface mold from the top of the substrate; and (3) a step of drying the hydrogel to remove the residual free water, thereby fabricating a vitrified dried hydrogel.

<21> The method for producing a dried hydrogel as set forth above in <20>, characterized in that in the step (1), a support is introduced into the hydrogel in the inside of the wall surface mold.

<22> The method for producing a dried hydrogel as set forth above in <20>, characterized in that in the step (1), the amount of the free water within the hydrogel is reduced to from about ¼ to ¾.

<23> The method for producing a dried hydrogel as set forth above in <20>, characterized in that in the step (3), the vitrification is conducted on a film a film possessing a capacity facilitating the detachability of the dried hydrogel.

<24> The method for producing a dried hydrogel as set forth above in <23>, characterized in that the film is Parafilm.

<25> A method for producing a dried hydrogel capable of being molded in a desired shape, characterized by including the following steps of:

(1) a step of keeping a hydrogel in the inside of a surface wall mold having an arbitrary shape, as disposed on a substrate on which a film a film possessing a capacity facilitating the detachability of the dried hydroge is laid, and discharging a part of free water within the hydrogel from a gap between the film on the substrate and the wall surface mold;

(2) a step of removing the wall surface mold from the top of the substrate; and (3) a step of drying the hydrogel to remove the residual free water, thereby fabricating a vitrified dried hydrogel.

<26> The method for producing a dried hydrogel as set forth above in <25>, characterized by after the step (3), including (4) a step of cutting the dried hydrogel superposed with the film in a desired shape.

<27> The method for producing a dried hydrogel as set forth above in <26>, characterized by after the step (4), including a step of releasing the dried hydrogel from the film.

<28> The method for producing a dried hydrogel as set forth above in <25>, characterized in that in the step (1), a support is introduced into the hydrogel in the inside of the wall surface mold.

<29> The method for producing a dried hydrogel as set forth above in <25>, characterized in that in the step (1), the amount of the free water within the hydrogel is reduced to from about ¼ to ¾.

<30> The method for producing a dried hydrogel as set forth above in <25>, characterized in that the film is Parafilm.

<31> A laminate, characterized in that the dried vitrigel membrane as set forth above in <1> is superposed and integrated.

<32> An equivalent of collagen constituting mainly a substance of a cornea using a laminate obtained by superposing plural sheets of vitrigel membranes in which the dried vitrigel membrane as set forth above in <1> is made of collagen as a raw material, and this dried vitrigel membrane is rehydrated.

<33> An equivalent of collagen constituting mainly a substance of a cornea using a vitrigel membrane obtained by rehydrating a laminate in which the dried vitrigel membrane as set forth above in <1> is made of collagen as a raw material, and this dried vitrigel membrane is superposed and integrated.

Advantage of the Invention

According to the present invention, it is possible to quickly mass-produce a dried hydrogel and a dried vitrigel membrane, each of which does not have an amorphous outer peripheral edge originating in the wall surface and has a desired shape.

In addition, by superposing a dried vitrigel membrane or a dried hydrogel on a releasable film, it is possible to release the dried vitrigel membrane or dried hydrogel from the film and freely handle it in a membrane state. Furthermore, it is possible to subject a vitrified dried vitrigel membrane or dried hydrogel to cutting work in an arbitrary form other than a shape of a wall surface mold.

MODES FOR CARRYING OUT THE INVENTION

A first embodiment of the production method of a dried hydrogel according to the present invention is concerned with a method for producing a dried hydrogel having a desired shape, which includes the following steps of:

(1) a step of keeping a hydrogel in the inside of a wall surface mold disposed on a substrate and having a shape the same as the desired shape and discharging a part of free water within the hydrogel from a gap between the substrate and the wall surface mold;

(2) a step of removing the wall surface mold from the top of the substrate; and (3) a step of drying the hydrogel to remove the residual free water, thereby fabricating a vitrified dried hydrogel.

Furthermore, a first embodiment of the production method of a dried vitrigel membrane according to the present invention is concerned with a method for producing a dried vitrigel membrane having a desired shape, which includes, subsequently to the foregoing step (3), (4) a step of rehydrating the dried hydrogel to fabricate a vitrigel membrane; and (5) a step of redrying the vitrigel membrane to remove free water, thereby fabricating a vitrified dried vitrigel membrane.

In the present invention, the "hydrogel" refers to a substance in which a polymer takes a network structure due to a chemical bond, and a large quantity of water is held in networks thereof, and more specifically, a substance obtained by introducing crosslinkage into a polymer derived from a natural product or a synthetic polymer made of artificial materials.

In addition, the "dried hydrogel" refers to material obtained by removing free water from the hydrogel to achieve vitrification. Furthermore, the "vitrigel membrane" is a material obtained by rehydrating this dried hydrogel. Incidentally, as described above, the "gel in a novel stable state which can be fabricated through a step of vitrification" is named the "vitrigel" by the present inventor. Then, the "dried vitrigel membrane" refers to a material obtained by again vitrifying this vitrigel. By rehydrating the dried vitrigel membrane as needed, the vitrigel membrane can be obtained.

Figure 1:
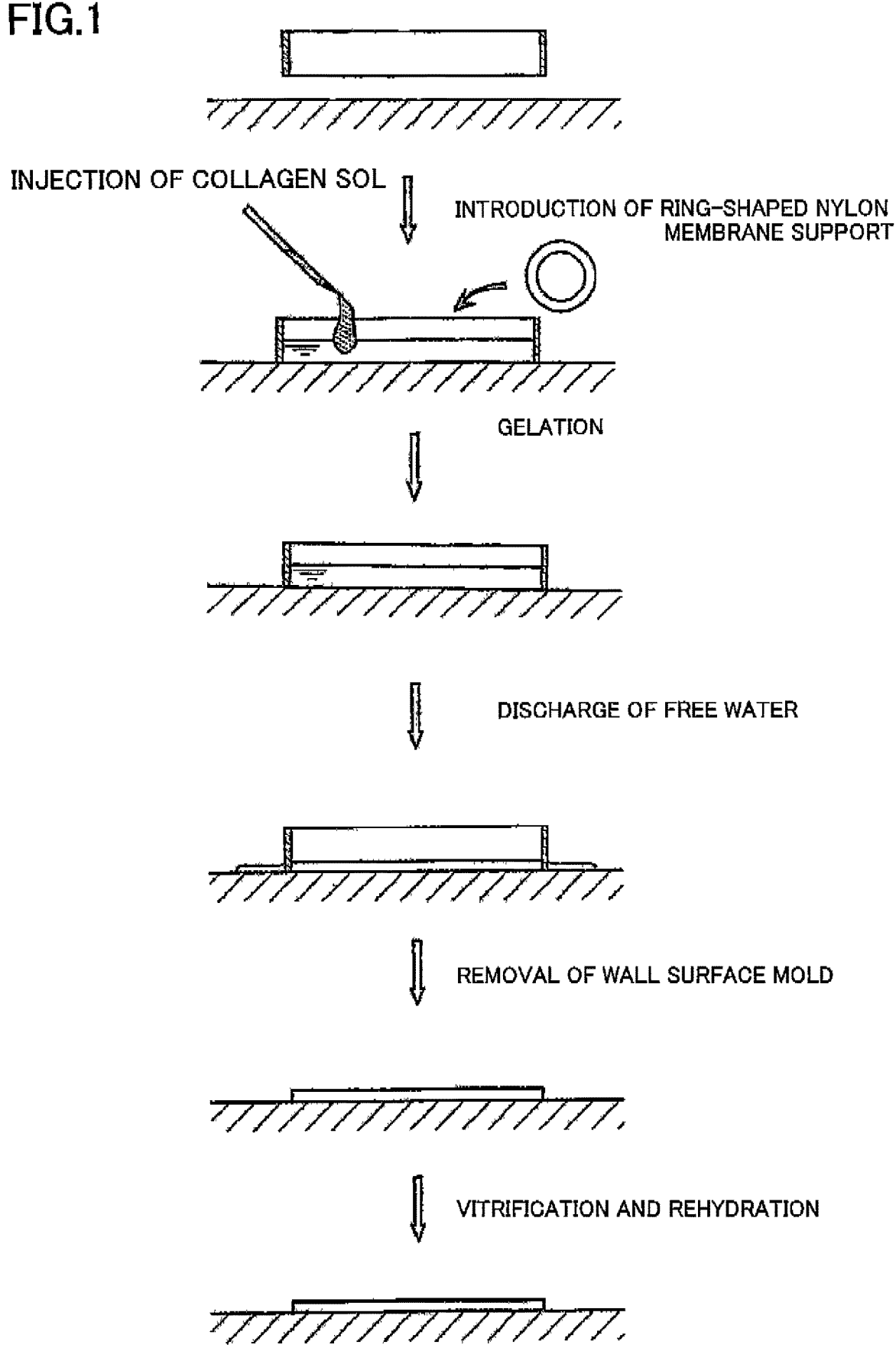
FIG. 1 is a flowchart illustrating an embodiment of a method for producing a vitrigel membrane according to the present invention.

Each of the steps is hereunder described. FIG. 1 is a flowchart illustrating an embodiment of the method for producing a vitrigel membrane according to the present invention.

Step (1): A hydrogel is kept in the inside of a wall surface mold disposed on a substrate and having a shape the same as the foregoing desired shape, and a part of free water within the hydrogel is discharged from a gap between the substrate and the wall surface mold.

As for the substrate and the wall surface mold, a material capable of enduring sterilization with 70% ethanol or by an autoclave or the like can be properly used. Specifically, there can be exemplified plastics such as polystyrene, acrylic resins, etc., glass, stainless steel, and the like.

Figure 2:
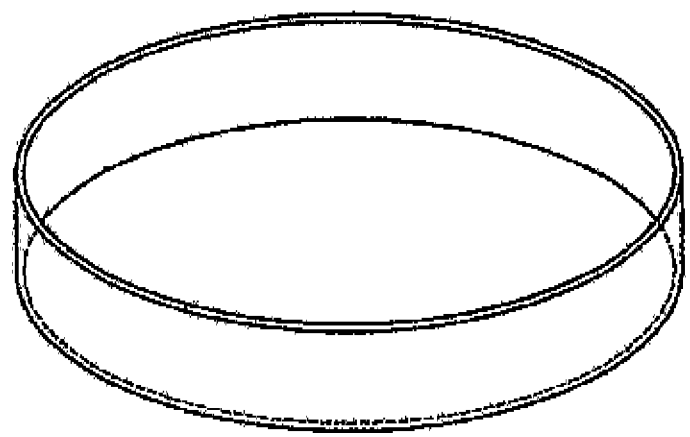
FIG. 2 is a perspective view illustrating a wall surface mold which is used in a method for producing a vitrigel membrane according to the present invention.
Figure 3:
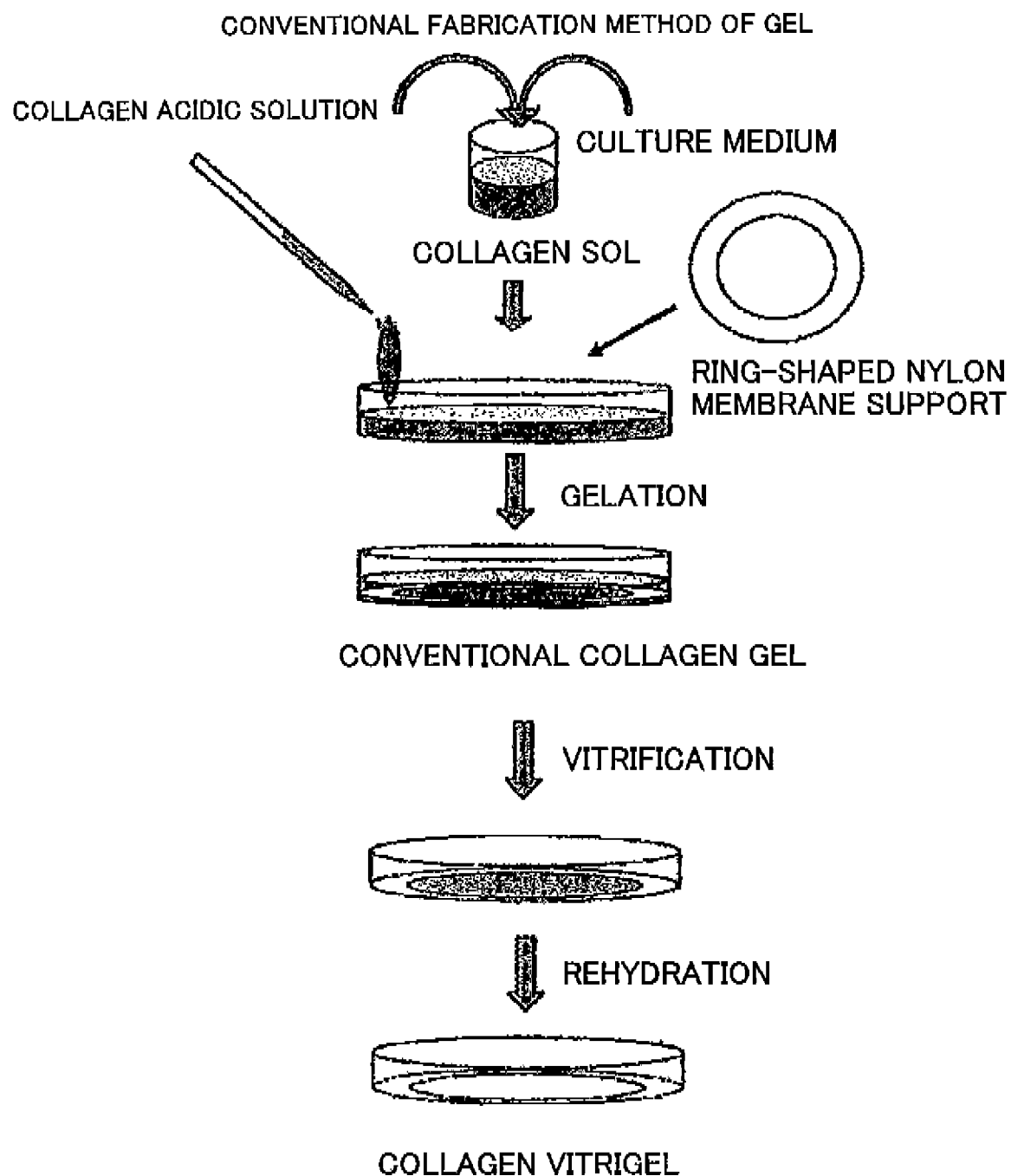
FIG. 3 is a flowchart illustrating an embodiment of a conventional method for producing a thin vitrigel membrane.

In the first embodiment, the wall surface mold can be formed in a cylindrical frame body not having a top surface and a bottom surface, and the shape of the wall surface mold can be designed to be identical with the desired shape of the vitrigel membrane. Specifically, for example, in the case of fabricating a circular vitrigel membrane, as illustrated in FIG. 2, a material in which a wall surface (frame) thereof is in a ring shape (in a cylindrical form) can be used. In addition, in the case of fabricating a rectangular vitrigel membrane, a material in which a wall surface (frame) thereof is in a rectangular shape (in a rectangular tube form) can be used.

Then, when the wall surface mold is disposed on the substrate, the both are in a contact state with each other. However, physically speaking, a slight gap is formed to an extent that free water can be discharged by asperity on the surfaces of the substrate and the wall surface mold. In the present invention, a number of wall surface molds can be disposed on the substrate corresponding to the desired number of vitrigel membranes.

In the present invention, examples of the polymer derived from a natural product as a raw material which is used for fabricating a hydrogel include collagen, a basement membrane component reconstructed with a mouse EHS tumor extract (a trade name: Matrigel), gelatin, agar, agarose, fibrin, glycosaminoglycan, hyaluronic acid, proteoglycan, and the like. It is possible to fabricate a hydrogel by choosing a component such as a salt, etc., a concentration thereof, a pH, and the like, which are optimum for gelation.

In addition, examples of the synthetic polymer which is used for fabricating a hydrogel include polyacrylamide, polyvinyl alcohol, methyl cellulose, polyethylene oxide, poly(2-hydroxyethyl methacrylate)/polycaprolactone, and the like. In addition, it is possible to fabricate a hydrogel using two or more kinds of these polymers. The amount of the hydrogel can be adjusted taking into consideration the thickness of the vitrigel membrane to be fabricated.

Above all, the raw material of the hydrogel is preferably collagen. In the case of using a collagen gel, a material obtained by injecting a collagen sol into a wall surface mold disposed on a substrate and incubating it to achieve gelation can be used. In FIG. 1, a collagen sol as a raw material of the hydrogel is illustrated.

When the case of using a collagen sol is explained as an example, the collagen sol can be prepared using, as a material having an optimum salt concentration, a physiological saline solution, PBS (phosphate buffered saline), HBSS (Hank's balanced salt solution), a basal culture medium, a serum-free culture medium, a serum-containing culture medium, or the like. In addition, the pH of the solution at the gelation of collagen is preferably from about 6 to 8.

Here, it is desirable to conduct the preparation of a collagen sol at 4° C. Thereafter, incubation at the time of gelation must be conducted at a temperature lower than the denaturation temperature of collagen which depends upon an animal species of collagen to be used. However, in general, the preparation can be conducted by keeping the temperature at a temperature which is not higher than 37° C. and at which the gelation can be achieved in from several minutes to several tens of minutes.

In addition, in the collagen sol, when the concentration of collagen is less than 0.2%, it is too low so that the gelation is insufficient, whereas when the concentration of collagen is more than 0.3%, it is too thick so that homogenization is difficult. Accordingly, the concentration of collagen in the collagen sol is preferably from 0.2 to 0.3%, and more preferably about 0.25%.

The thus adjusted collagen sol is injected into the inside of the wall surface mold. Since the collagen sol having the foregoing concentration is viscous, so far as the collagen sol is injected into the inside of the wall surface mold, and incubation is quickly conducted, the collagen sol can be gelled within several minutes without being discharged from a gap between the substrate and the wall surface mold.

Then, the formed collagen gel adheres closely to the substrate and the wall surface mold. However, when it is allowed to stand for a prescribed time, a part of free water within the collagen gel is discharged to the outside of the wall surface mold from a gap between the substrate and the wall surface mold with a lapse of time.

Here, by slightly moving the wall surface mold in the vertical direction or the like, the adhesion between the gel and the wall surface mold is unfastened to produce a slight gap, and therefore, the discharge of free water can be promoted.

Furthermore, for example, in the case where the amount of the 0.25% collagen sol which is injected per unit area (1.0 cm$^2$) is 0.4 mL or more, it is desirable to remove the free water discharged from a gap between the substrate and the wall surface mold with a lapse of time until the amount of the free water within the gelled collagen gel is reduced to from about ¼ to ⅔. According to this, the collagen concentration of the gel becomes from about 0.375 to 1.0%, and therefore, even when the wall surface mold is removed, the gel strength can be attained to an extent that the gel shape is not warped. Incidentally, thereafter, the vitrification can be achieved by naturally drying the free water remaining within the gel in a state of being also entrained with free water discharged onto the top of the substrate and removing it. Here, from the viewpoint of quick mass production, the time for reducing the amount of the free water within the collagen gel to from about ¼ to ⅔ is desirably from 2 to 8 hours. Furthermore, thereafter, the time for naturally drying the free water remaining within the gel to completely remove it is desirably not more than 48 hours. For that purpose, the amount of the 0.25% collagen sol to be injected per unit area (1.0 cm$^2$) is desirably from 0.1 to 2.4 mL. As a result, it is possible to fabricate a collagen vitrigel membrane containing collagen in an amount of from 250 μg to 6 mg per unit area (1.0 cm$^2$).

Incidentally, as a method for fabricating a collagen vitrigel membrane containing a larger amount of collagen per unit area, the following two methods are possible. A first method is a method of superposing a collagen sol on the already fabricated collagen vitrigel membrane or its dried material to achieve gelation, followed by vitrification and rehydration. By repeating this method, a laminate having a collagen vitrigel membrane superposed therein is obtained, whereby it becomes possible to fabricate a collagen vitrigel membrane (laminate) having an arbitrary thickness. In addition, a second method is a method of imbedding the already fabricated collagen vitrigel membrane or its dried material within the collagen sol to achieve gelation, followed by vitrification and rehydration. In this method, a laminate in which an arbitrary number of sheets of collagen vitrigel membranes are superposed in an imbedded state is obtained, too, whereby it becomes possible to fabricate a collagen vitrigel membrane having an arbitrary thickness. Incidentally, it is also possible to fabricate a vitrigel membrane having different components on the back and front sides or in a stratiform state by using other components than collagen to the sol for superposition used in the first method and the sol used for imbedding in the second method.

In addition, a support can be introduced into a hydrosol in the inside of the wall surface mold. Examples of the support include a nylon membrane, a wire, a cotton-made gauze, a silk thread, other weaves, bioabsorbable material, and the like, and materials adaptive to the shape of the inside of the wall surface mold can be used. Preferably, in the case where the wall surface mold is in a ring form, the support can be made of a ring-shaped nylon membrane having an outer diameter substantially equal to an inner diameter of the wall surface mold illustrated in FIG. 1. By introducing the support into the sol, the strength or shape-retaining ability of the vitrigel membrane increases, and the handling properties and convenience are enhanced. For example, by introducing a ring-shaped nylon membrane support having an outer circle diameter shorter by about 1.0 mm than a diameter of a circular wall surface mold, it is possible to fabricate a vitrigel membrane capable of being easily handled by tweezers.

Step (2): The wall surface mold is removed from the top of the substrate.

The wall surface mold is removed while leaving the hydrogel on the substrate. In the hydrogel, since the free water is discharged, the shape which is held by the wall surface mold can be maintained without causing deformation or the like on the substrate.

Step (3): The hydrogel is dried to remove the residual free water, thereby fabricating a vitrified dried hydrogel.

If desired, the hydrogel is moved into a container in which it is intended to finally vitrify the hydrogel, and thereafter, the free water within the hydrogel is completely removed by means of drying to achieve vitrification. For example, by moving the hydrogel onto a film possessing a capacity facilitating the detachability of the dried hydrogel, it is possible to release the fabricated dried hydrogel from the film. In addition, in that case, the dried hydrogel can also be molded in a desired shape on the film. Examples of the film include non-water-absorbing films such as Parafilm, Saran Wrap, a polyvinyl resin, etc. In particular, Parafilm is preferable.

By making the period of this vitrification step longer, it is possible to obtain a vitrigel membrane having excellent transparency and strength at the time of rehydration. Incidentally, if desired, the vitrigel membrane obtained by means of vitrification for a short period of time and subsequent rehydration can also be rinsed with PBS or the like and again vitrified.

As the drying method, various methods, for example, air drying, drying in a closed container (by circulating air within the container and always supplying dry air), drying in an atmosphere having a silica gel placed therein, and the like, can be adopted. Examples of the air drying method include methods such as drying in an incubator kept in a sterilized state at 10° C. and at a humidity of 40 for 2 days, drying in a clean bench in a sterilized state at room temperature overnight, etc.

The dried hydrogel can be industrially effectively utilized because it can be fabricated into a vitrigel membrane by means of rehydration as needed. In addition, as described later, the vitrigel membrane obtained by rehydrating the dried hydrogel according to the present invention is also excellent from the standpoint that an unnecessary vitrigel membrane originating in the wall surface (called "amorphous outer peripheral edge" in the present invention) is not entrained.

Furthermore, in the production method of a dried vitrigel membrane according to the present invention, in the step (4), the dried hydrogel is rehydrated to fabricate a vitrigel membrane.

By rehydrating the dried hydrogel with PBS, the used culture medium, or the like, it is possible to fabricate the vitrigel membrane. Here, the liquid for rehydration may contain various components such as physiologically active substances, etc. Examples of the physiologically active substance include various pharmaceuticals inclusive of antibiotics, cell growth factors, differentiation-inducing factors, cell adhesion factors, antibodies, enzymes, cytokines, hormones, lectin, and extracellular matrix components which are not gelled, such as fibronectin, vitronectin, entactin, osteopoietin, etc. In addition, it is also possible to contain a plurality of these components.

Step (5): The vitrigel membrane is redried to remove the free water, thereby fabricating a vitrified dried vitrigel membrane.

As the drying method, similar to the step (3), various methods, for example, air drying, drying in a closed container (by circulating air within the container and always supplying dry air), drying in an atmosphere having a silica gel placed therein, and the like, can be adopted.

By redrying the vitrigel membrane, it is possible to fabricate the vitrified dried vitrigel membrane. This dried vitrigel membrane can be again converted into a vitrigel membrane by means of rehydration as needed.

In addition, the vitrigel membrane can also be vitrified on a film possessing a capacity facilitating the detachability of the dried vitrigel membrane, for example, Parafilm. The Parafilm is a thermoplastic film made of a paraffin as a raw material and has such characteristic features that it has stretchability and stickiness and is excellent in airtightness and waterproofness.

By superposing the dried vitrigel membrane on the film possessing a capacity facilitating the detachability of the dried vitrigel membrane, it is possible to release the dried collagen vitrigel membrane from the film and freely handle it in a membrane state. Furthermore, it is possible to subject the vitrified dried vitrigel membrane to cutting work in an arbitrary form other than the shape of the wall surface mold.

Incidentally, the components contained in the "dried hydrogel" and the "dried vitrigel membrane" are not always identical with each other. The "dried hydrogel" contains the components of the hydrogel, whereas the "dried vitrigel membrane" contains the components remaining in the vitrigel membrane equilibrated with the aqueous solution at the time of rehydration of the dried hydrogel.

In addition, the vitrigel membrane obtained by rehydration of the dried vitrigel membrane in the step (5) is longer in the period of vitrification than the vitrigel membrane obtained in the step (4), and hence, it is excellent in strength and transparency.

Furthermore, it is possible to prolong the period of vitrification in a state of the "dried hydrogel". However, the "dried hydrogel" is in a state where all of the components at the time of fabricating a hydrogel are co-existent, and components which are unnecessary at the time of continuously maintaining the dried hydrogel or at the time of utilizing the vitrigel membrane are also intermingled. On the other hand, with respect to the vitrigel membrane after removing the unnecessary intermingled components by rehydrating the "dried hydrogel", the unnecessary components are also removed in its dried material. Accordingly, when it is necessary to keep the period of vitrification long, it is preferable to continuously maintain this state of a dried vitrigel membrane, and such is excellent from the standpoint that the unnecessary components are not intermingled in the vitrigel membrane obtained by rehydrating the dried vitrigel membrane.

In the first embodiment of the present invention, the shape of the wall surface mold is designed to be identical with the desired shape of the vitrigel membrane. Furthermore, after discharging free water in an amount of from about ¼ to ¾ from a gap between the substrate and the wall surface mold, the wall surface mold is removed, and vitrification is conducted by means of drying. Therefore, it is possible to obtain a vitrigel membrane having a desired shape reflecting the shape of the wall surface mold. That is, as described above, in the conventional method using a culture Petri dish, the unnecessary thin vitrigel membrane originating in the wall surface of the culture Petri dish (called "amorphous outer peripheral edge" in the present invention) was entrained. However, in the present invention, it is possible to obtain a dried hydrogel or a dried vitrigel membrane not having an amorphous outer peripheral edge and reflecting the shape of the wall surface mold on the substrate. Accordingly, an operation for removing the amorphous outer peripheral edge which was conventionally required is unnecessary, and it is possible to quickly mass-produce a vitrigel membrane. Furthermore, since the amount of free water is reduced to from about ¼ to ¾ by utilizing the wall surface mold, it is possible to shorten the drying time for removing free water, which hitherto generally required two days or more, to a time of from about ½ to ¼. Such shortening of the drying time greatly contributes to the quick mass production of a dried vitrigel membrane, too.

In addition, conventionally, two or more days were required for the drying time, and therefore, for the purpose of suppressing the drying time to a practical range, the injection amount of a hydrogel was limited. Accordingly, the vitrigel film was fabricated in a thin membrane state (thin vitrigel membrane) in a thickness of about 120 μm at maximum (Non-Patent Document 2). On the other hand, in the vitrigel membrane according to the present invention, since the drying time for removing free water can be shortened to a time of from about ½ to ¼, even when the drying time is suppressed to a practical range, the injection amount of a hydrogel can be increased as compared with that of the prior art. Specifically, in the present invention, it is possible to easily fabricate a vitrigel membrane having a thickness of about 1 mm for a practical drying time of from about 2 to 3 days.

Furthermore, the vitrigel membrane and the dried vitrigel membrane can also be fabricated by, for example, mixing the sol solution prior to the gelation with physiologically active substances which are intended to be contained and then going through a fabrication step of a vitrigel membrane, including gelation, vitrification, and the like.

In the vitrigel membrane and the dried vitrigel membrane each containing physiologically active substances, necessary factors for adhesion, growth, and differentiation of cells, and the like can be supplied from the vitrigel membrane side, and hence, a better culture environment can be realized. In addition, the vitrigel membrane and the dried vitrigel membrane are very useful for conducting a test for examining influences of the contained physiologically active substances against cells. In addition, the vitrigel membrane containing physiologically active substances may also function as a drug delivery system by means of transplantation into the body (Non-Patent Document 3).

Furthermore, in the vitrigel membrane fabricated by the method according to the present invention, it is possible to allow a physiologically active substance having a large molecular weight to pass therethrough. According to this, the vitrigel membrane fabricated by the method according to the present invention is able to greatly contribute to tests and researches regarding an interaction via physiologically active substances between respective cells seeded on the two different surfaces of this vitrigel membrane (Non-Patent Document 3).

In addition, the vitrigel membrane fabricated by the method according to the present invention can be inserted into a culture container and used as a cell culture carrier for culturing animal cells. Examples of the animal cell to be cultured include primary cultured cells, established cells, fertilized eggs, and cells obtained by introducing a foreign gene into the foregoing cells. Furthermore, such cells may be undifferentiated stem cells, cells in the course of differentiation, terminally differentiated cells, or dedifferentiated cells. In addition, as the means for starting the culture of such cells, there is exemplified seeding with a cell suspension, a tissue explant, a fertilized egg, or a three-dimensionally reconstructed gel culture or multicellular aggregate (spheroid). Namely, it is possible to culture adhesive cells which can be cultured by the existing methods on the present vitrigel membrane.

Furthermore, for example, it is possible to culture at least one kind of the above-described cells on not only one surface but both surfaces of the vitrigel membrane. In the culture on the both surfaces, it is possible to culture cells of a different kind from each other on the respective surfaces. In particular, it becomes possible to undergo cell function assays having an epithelial-mesenchymal interaction, such as a percutaneous absorption model, an intestinal absorption model, etc., by culturing epithelial cells on one surface of the vitrigel membrane and mesenchyme cells on the other surface, respectively, or cell function assays such as a neovascularization model, a cancer infiltration model, etc. by culturing endothrial cells on one surface and cancer cells on the other surface, respectively.

Furthermore, in the case of increasing the thickness of one sheet of a vitrigel membrane, the transparency of the vitrigel membrane decreases in proportion to the thickness. In the case of superposing plural sheets of vitrigel membranes to make substantially the same thickness, the transparency is higher than that in one sheet of the vitrigel membrane. Accordingly, by superposing plural sheets of collagen vitrigel membranes to enhance the transparency and, for example, culturing cells derived from a cornea on this collagen vitrigel membrane, or the like, the resultant can be utilized as an equivalent of cornea. This equivalent of cornea can be transplanted in a living body and can also be utilized as a cornea model for various pharmacological tests.

Incidentally, as a method for fabricating an integrated laminate by superposing plural sheets of collagen vitrigel membranes, the following two methods (a repetition method and an insertion method) are possible. According to the repetition method, by injecting a collagen sol onto the already fabricated dried collagen vitrigel membrane and repeating gelation, vitrification, and rehydration, an integrated laminate can be fabricated. On the other hand, according to the insertion method, by inserting plural sheets of the previously fabricated collagen vitrigel membranes or dried collagen vitrigel membranes into a collagen sol, followed by vitrification and rehydration, an integrated laminate can be fabricated.

Next, a second embodiment of the production method of each of a dried hydrogel and a dried vitrigel membrane according to the present invention is described. With respect to points which are common to those in the first embodiment, a part of explanations thereof is hereunder omitted.

The second embodiment of the production method of a dried hydrogel according to the present invention is concerned with a method for producing a dried hydrogel having a desired shape, which includes the following steps of:

(1) a step of keeping a hydrogel in the inside of a surface wall mold having an arbitrary shape, as disposed on a substrate on which a film possessing a capacity facilitating the detachability of the dried vitrigel membrane is laid, and discharging a part of free water within the hydrogel from a gap between the film on the substrate and the wall surface mold;

(2) a step of removing the wall surface mold from the top of the substrate; and (3) a step of drying the hydrogel to remove the residual free water, thereby fabricating a vitrified dried hydrogel.

In this embodiment, the wall surface mold can also be formed in a cylindrical frame body not having a top surface and a bottom surface. However, its shape is arbitrary, and it is not necessary that the shape is identical with the desired shape of the dried hydrogel.

Then, in the second embodiment, a film possessing a capacity facilitating the detachability of the dried hydrogel is previously laid on a substrate, a sol is injected onto this film, and gelation and vitrification by means of drying are conducted. Examples of the film from which the dried hydrogel can be released include non-water-absorbing films such as Parafilm, Saran Wrap, a polyvinyl resin, etc. In particular, Parafilm is preferable.

In the second embodiment, the hydrogel is dried on the film to remove the residual free water, whereby a vitrified dried hydrogel can be fabricated. In that case, a dried hydrogel superposed with the film is obtained.

Since the dried hydrogel is adsorbed on and superposed with the film, it has high stability and can be easily cut in a desired shape. It is possible to subject the dried hydrogel to cutting work in an arbitrary shape other than the shape of the wall surface mold. Accordingly, in this embodiment, subsequently to the foregoing step (3), a step of cutting the dried hydrogel superposed with the film in a desired shape can be included.

Furthermore, in this embodiment, a step of releasing the dried hydrogel cut in a desired shape from the film can be included. By releasing the dried hydrogel from the film, it is possible to freely handle it in a membrane state. Furthermore, this dried hydrogel does not have an amorphous outer peripheral edge, either. Incidentally, it is also possible to subject the dried hydrogel released from the film to cutting work.

Then, by rehydrating the dried hydrogel molded in a desired shape, it is possible to obtain a vitrigel membrane having a desired shape.

Furthermore, the second embodiment of the production method of a dried vitrigel membrane according to the present invention is concerned with a method for producing a dried vitrigel membrane capable of being molded in a desired shape, which includes the following steps of:

(1) a step of keeping a hydrogel in the inside of a surface wall mold having an arbitrary shape, as disposed on a substrate on which a film possessing a capacity facilitating the detachability of the dried hydrogel is laid, and discharging a part of free water within the hydrogel from a gap between the film on the substrate and the wall surface mold;

(2) a step of removing the wall surface mold from the top of the substrate;

(3) a step of drying the hydrogel to remove the residual free water, thereby fabricating a vitrified dried hydrogel;

(4) a step of rehydrating the dried hydrogel to fabricate a vitrigel membrane; and (5) a step of redrying the vitrigel membrane to remove free water, thereby fabricating a vitrified dried vitrigel membrane.

By rehydrating the dried hydrogel superposed with the film, as obtained in the foregoing step (3), it is possible to obtain a vitrigel membrane superposed with the film (step (4)). By again drying this vitrigel membrane in a state of being superposed with the film to achieve vitrification, it is possible to obtain a dried vitrigel membrane superposed on the film (step (5)).

Since the dried vitrigel membrane fabricated in this embodiment does not have an amorphous outer peripheral edge, either, an operation for removing the amorphous outer peripheral edge which was conventionally required is unnecessary, and it is possible to quickly mass-produce a vitrigel membrane.

Furthermore, hitherto, there was involved such a problem that it is difficult to subject a vitrigel membrane to cutting work in a desired shape. However, even when the dried vitrigel membrane in a state of being adsorbed on and superposed with the film has a complicated shape, it can be subjected to precise cutting work in a desired shape. Accordingly, in this embodiment, a step of cutting the dried vitrigel membrane superposed with the film in a desired shape can be included. By rehydrating the dried vitrigel membrane molded in a desired shape as needed, it is possible to obtain a vitrigel membrane having a desired shape. Since it is possible to produce a vitrigel membrane having a desired shape depending upon an application, the convenience is further enhanced.

Incidentally, as has been described in the second embodiment of the production method of a dried hydrogel, in this embodiment, it is also possible to mold the dried hydrogel superposed on the film in a desired shape. Even in that case, by subsequently going through the foregoing steps (4) and (5), it is possible to fabricate a dried vitrigel membrane having a desired shape.

In addition, it is possible to easily release the dried vitrigel membrane superposed on the film from the film. Accordingly, it is possible to release the dried vitrigel membrane molded in a desired shape from the film and handle it in a membrane state. Accordingly, not only the dried vitrigel membrane is excellent in handling properties, but an effective application thereof to medical materials and the like utilizing its characteristics such as moisture absorption properties, etc. is expected.

EXAMPLE

The present invention is hereunder described in more detail by reference to the following Examples, but it should be construed that the present invention is not limited to these Examples at all.

Example 1

Fabrication of Ring-Shaped Nylon Membrane Support-Provided Dried Collagen Vitrigel Membrane (Collagen Amount: 0.55 to 2.2 Mg/$Cm^2$) Utilizing Substrate and Wall Surface Mold A 0.25% sol of bovine skin-derived type I collagen was prepared by uniformly mixing equal amounts of a 0.5% type I collagen acidic solution (KOKEN #IAC-50: 5 mg/mL) and a cell culture medium within a sterilized conical tube having a capacity of 50 mL (Falcon #35-2070) cooled on ice. Incidentally, the cell culture medium as used herein is a Dulbecco's modified Eagle's culture medium (GIBCO BRL #11885-084) containing 10% inactivated fetal calf serum (SIGMA #F2442), 20 mM of HEPES (GIBCO BRL #15630-080), 100 units/mL of penicillin, and 100 μg/mL of streptomycin (GIBCO BRL #15140-148).

The ring-shaped nylon membrane support was fabricated by cutting out a nylon membrane (GE Healthcare #RPN1732B; Hybond-N+, nucleic acid blotting membrane) so as to have a diameter of an outer circle of 33 mm and a diameter of an inner circle of 24 mm, subjected to a sterilization treatment with 70% ethanol for 10 minutes, rinsing three times with sterilized PBS for 10 minutes, and further equilibrating with the foregoing cell culture medium for 10 minutes (see FIG. 1 of Patent Document 2).

A bottom surface of a hydrophobic polystyrene-made culture Petri dish with a diameter of 60 mm (Falcon #35-1007) was used as a substrate. In addition, an acrylic resin-made mold with a diameter of an outer circle of 38 mm, a diameter of an inner circle of 34 mm, and a height of 10.0 mm was used as a wall surface mold. In addition, the wall surface mold was used after subjecting to a sterilization treatment by spraying 70% ethanol and then wiping off it. Specifically, one wall surface mold was placed on one substrate, thereby fabricating one container capable of separating the substrate and the wall surface mold from each other.

A collagen gel was fabricated by inserting one sheet of the ring-shaped nylon membrane support into this container, immediately thereafter injecting 2.0 mL, 4.0 mL, 6.0 mL, or 8.0 mL of the 0.25% collagen sol, and covering the substrate with a lid of the Petri dish, followed by gelation within a moisturized incubator at 37.0° C. in the presence of 5.0% of $CO_2$ and 95% of air. On that occasion, the injected collagen sol was gelled without being discharged from a gap between the substrate and the wall surface mold. At the two-hour period, four-hour period, six-hour period, and eight-hour period after transferring into the moisturized incubator at 37.0° C., not only the amount of free water within the collagen gel which was discharged to the outside of the wall surface mold from the gap between the substrate and the wall surface mold was quantitatively determined, but the discharged free water at the every-hour period was removed. Incidentally, at the two-hour period, the wall surface mold was slightly moved in the vertical direction, thereby unfastened the adhesion between the collagen gel and the wall surface mold.

As a result, it was noted that in all of the collagen gels, the free water was discharged to the outside of the wall surface mold in a proportion of ⅓ or more at the four-hour period and about ⅔ at the eight-hour period, respectively (Table 1).

The time required for the natural drying was greatly shortened as compared with that by the conventional method (the following Comparative Example 1).

At the day 1 or day 2 after the vitrification, the dried collagen gel was transferred into a clean bench at room temperature, and it was rehydrated by the addition of 5.0 mL of PBS within the Petri dish of the substrate and released from the substrate, thereby fabricating a ring-shaped nylon membrane support-provided collagen vitrigel membrane. Then, by rinsing with 5.0 mL of PBS several times, a ring-shaped nylon membrane support-provided collagen vitrigel membrane equilibrated with PBS was fabricated. This ring-shaped nylon membrane support-provided collagen vitrigel membrane reflected the shape of the inner circle (area: 9.1 cm$^2$) with a diameter of 34 mm of the wall surface mold and imbedded the periphery of the outer circle with a

TABLE 1

| Injection amount of 0.25% collagen sol (collagen amount) | Accumulated discharge amount up to the two-hour period after gelation | Accumulated discharge amount up to the four-hour period after gelation | Accumulated discharge amount up to the six-hour period after gelation | Accumulated discharge amount up to the eight-hour period after gelation |
|---|---|---|---|---|
| 2.0 mL (5.0 mg) | 0.23 mL (11.5%) | 0.81 mL (40.5%) | 1.09 mL (54.5%) | 1.22 mL (61.0%) |
| 4.0 mL (10.0 mg) | 0.25 mL (6.25%) | 1.61 mL (40.3%) | 2.23 mL (55.8%) | 2.68 mL (67.0%) |
| 6.0 mL (15.0 mg) | 0.90 mL (15.0%) | 2.70 mL (45.0%) | 3.72 mL (62.0%) | 4.33 mL (72.2%) |
| 8.0 mL (20.0 mg) | 1.62 mL (20.3%) | 3.87 mL (48.4%) | 5.18 mL (64.8%) | 5.97 mL (74.6%) |

Incidentally, the wall surface mold was removed from the top of the substrate at the eight-hour period. On that occasion, the wall surface mold was in a non-adhered state to the collagen gel, and attachment of the collagen gel to the surroundings such as an inner wall of the wall surface mold removed from the top of the substrate, etc. was not observed at all. In addition, at the eight-hour period, the collagen gel was transferred into a clean bench under a condition at 10.0° C. and at a humidity of 40% from the moisturized incubator at 37.0° C. Thereafter, the free water remaining within the collagen gel was completely removed by means of natural drying in a state where the lid of the Petri dish was removed, thereby obtaining a vitrified dried collagen gel. Here, the vitrification starts from the stage at which the free water remaining within the collagen gel has been completely removed. Then, an approximate time required for the natural drying until this vitrification started was measured. As a result, the time required until the vitrification started (until the free water remaining within the collagen gel was completely removed to form a dried collagen gel) was not more than 21 hours in the case of 2.0 mL and 4.0 mL of the 0.25% collagen gel and 21 hours or more and not more than 41 hours in the case of 6.0 mL and 8.0 mL of the 0.25% collagen gel, respectively (Table 2).

TABLE 2

Figure 4:
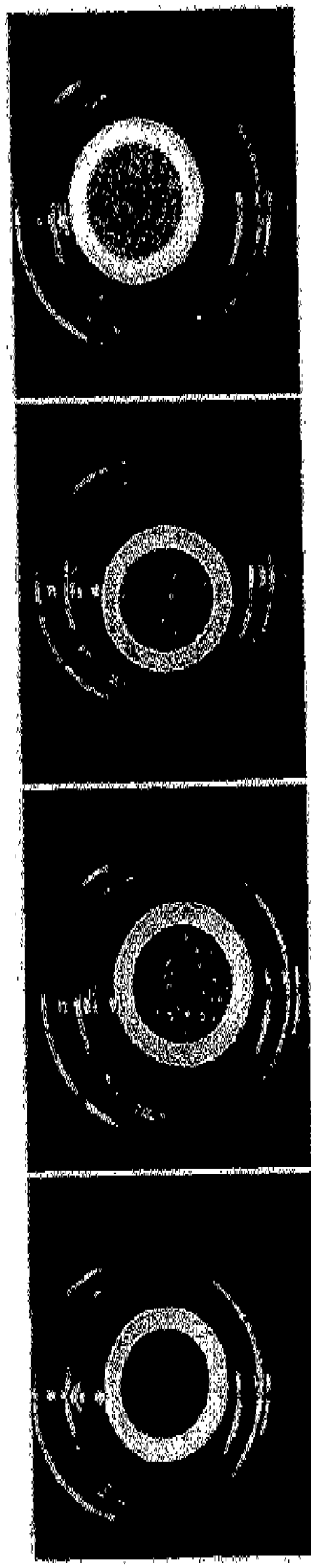
FIG. 4 is a view illustrating a collagen vitrigel membrane not having an amorphous outer peripheral edge.

| Injection amount of 0.25% collagen sol (collagen amount) | Amount of free water remaining within the gel at the eight-hour period after gelation | Time required for drying residual free water |
|---|---|---|
| 2.0 mL (5.0 mg) | 0.78 mL (39.0%) | Not more than 21 hours |
| 4.0 mL (10.0 mg) | 1.32 mL (33.0%) | Not more than 21 hours |
| 6.0 mL (15.0 mg) | 1.67 mL (27.8%) | 21 hours or more and not more than 41 hours |
| 8.0 mL (20.0 mg) | 2.03 mL (25.4%) | 21 hours or more and not more than 41 hours | diameter of 33 mm of the ring-shaped nylon membrane support with a slight clearance therein (FIG. 4).

Incidentally, this ring-shaped nylon membrane support-provided collagen vitrigel membrane contains collagen in an amount of 5.0 mg (derived from 2.0 mL of the collagen sol), 10.0 mg (derived from 4.0 mL of the collagen sol), 15.0 mg (derived from 6.0 mL of the collagen sol), and 20.0 mg (derived from 8.0 mL of the collagen sol), respectively from the left-hand side of FIG. 4.

Furthermore, these ring-shaped nylon membrane support-provided collagen vitrigel membranes were transferred into a hydrophilic polystyrene-made culture Petri dish with a diameter of 35 mm (Falcon #35-3001) and a hydrophobic polystyrene-made culture Petri dish with a diameter of 60 mm, in which Parafilm (manufactured by Pechiney Plastic Packaging) was laid on the bottom surface thereof (Falcon #35-1007), respectively and allowed to stand for complete drying for about 1 to 2 days within a clean bench under a condition at 10.0° C. and at a humidity of 40% in a state where a lid thereof was removed. Thereafter, each of the Petri dishes was transferred into a clean bench at room temperature and covered by a lid. Thereafter, each of the Petri dishes was sterilely stored and maintained at room temperature to allow the vitrification to proceed, thereby fabricating respective ring-shaped nylon membrane support-provided dried collagen vitrigel membranes.

As a result, the former ring-shaped nylon membrane support-provided dried collagen vitrigel membrane fabricated within the hydrophilic polystyrene-made culture Petri dish with a diameter of 35 mm adhered closely to the bottom surface of the Petri dish and could not be released in the dried state; however, after rehydration, it could be easily released from the bottom surface of the Petri dish by using tweezers without requiring an operation of tracing the inner wall of the Petri dish along the periphery by tweezers with sharp tips and in a state where an excessive vitrigel membrane (amorphous outer peripheral edge) was not entrained on the outer periphery of the ring-shaped nylon membrane. Accordingly, this ring-shaped nylon membrane support-provided dried collagen vitrigel membrane is excellent in handling properties and useful as a carrier on the both surfaces of which cells are three-dimensionally cultured.

The latter ring-shaped nylon membrane support-provided dried collagen vitrigel membrane fabricated on Parafilm was in a state where it was adsorbed onto the Parafilm and could be easily released in a dried state from the Parafilm. Accordingly, the ring-shaped nylon membrane support-provided dried collagen vitrigel membrane adsorbed onto the Parafilm or the ring-shaped nylon membrane support-provided dried collagen vitrigel membrane released from the Parafilm is excellent in handling properties and useful as a biomaterial.

Incidentally, this ring-shaped nylon membrane support-provided dried collagen vitrigel membrane contains collagen in an amount of 0.55 mg (derived from 2.0 mL of the collagen sol), 1.1 mg (derived from 4.0 mL of the collagen sol), 1.6 mg (derived from 6.0 mL of the collagen sol), or 2.2 mg (derived from 8.0 mL of the collagen sol) per unit area (1.0 cm$^2$).

Incidentally, in the foregoing step, if the ring-shaped nylon membrane is not inserted, a ring-shaped nylon membrane support-free dried collagen vitrigel membrane can be fabricated. In addition, if the bottom planar surface shape and height of the wall surface mold are modified, a dried collagen vitrigel membrane having arbitrary shape and thickness can be fabricated.

Comparative Example 1

Fabrication of Ring-Shaped Nylon Membrane Support-Provided Dried Collagen Vitrigel Membrane Utilizing Conventional Culture Petri Dish Experiments were conducted in the same manner as that in Example 1, except that a conventional hydrophobic polystyrene-made culture Petri dish (Falcon #35-1008) with a diameter of 35 mm was used instead of utilizing the wall surface mold capable of be separated from the substrate in Example 1.

Specifically, a collagen gel was fabricated by inserting one sheet of the ring-shaped nylon membrane support into this culture Petri dish, immediately thereafter injecting 2.0 mL, 4.0 mL, 6.0 mL, or 8.0 mL of the 0.25% collagen sol, and covering it with a lid of the Petri dish, followed by gelation within a moisturized incubator at 37.0° C. in the presence of 5.0% of $CO_2$ and 95% of air. At the two-hour period, four-hour period, six-hour period, and eight-hour period after transferring into the moisturized incubator at 37.0° C., not only the amount of free water having oozed out on the upper surface side of the collagen gel was quantitatively determined, but the oozed-out free water at the every-hour period was removed. As a result, it was noted that in all of the collagen gels, only not more than 10% of the free water oozed out on the upper surface side at the eight-hour period (Table 3).

TABLE 3

| Injection amount of 0.25% collagen sol (collagen amount) | Accumulated discharge amount up to the two-hour period after gelation | Accumulated discharge amount up to the four-hour period after gelation | Accumulated discharge amount up to the six-hour period after gelation | Accumulated discharge amount up to the eight-hour period after gelation |
| --- | --- | --- | --- | --- |
| 2.0 mL (5.0 mg) | 0 mL (0%) | 0.01 mL (0.5%) | 0.02 mL (1.0%) | 0.02 mL (1.0%) |
| 4.0 mL (10.0 mg) | 0.05 mL (1.3%) | 0.10 mL (2.5%) | 0.16 mL (4.0%) | 0.21 mL (5.3%) |
| 6.0 mL (15.0 mg) | 0.07 mL (1.2%) | 0.20 mL (3.3%) | 0.32 mL (5.3%) | 0.38 mL (6.3%) |
| 8.0 mL (20.0 mg) | 0.32 mL (4.0%) | 0.58 mL (7.3%) | 0.66 mL (8.3%) | 0.70 mL (8.8%) |

In addition, at the eight-hour period, the collagen gel was transferred into a clean bench under a condition at 10.0° C. and at a humidity of 40% from the moisturized incubator at 37.0° C. Thereafter, the free water remaining within the collagen gel was completely removed by means of natural drying in a state where the lid of the Petri dish was removed, thereby obtaining a vitrified dried collagen gel.

Here, the vitrification starts from the stage at which the free water remaining within the collagen gel has been completely removed. Then, an approximate time required for the natural drying until this vitrification started (until the free water remaining within the collagen gel was completely removed to form a dried collagen gel) was measured. As a result, the time required until the vitrification started was 21 hours or more and not more than 41 hours in the case of 2.0 mL of the 0.25% collagen gel, 41 hours or more and not more than 48 hours in the case of 4.0 mL of the 0.25% collagen gel, 48 hours (2 days) or more and not more than 3 days in the case of 6.0 mL of the 0.25% collagen gel, and 3 days or more and not more than 4 days in the case of 8.0 mL of the 0.25% collagen gel, respectively (Table 4).

TABLE 4

| Injection amount of 0.25% collagen sol (collagen amount) | Amount of free water remaining within the gel at the eight-hour period after gelation | Time required for drying residual free water |
| --- | --- | --- |
| 2.0 mL (5.0 mg) | 1.98 mL (99.0%) | 21 hours or more and not more than 41 hours |
| 4.0 mL (10.0 mg) | 3.79 mL (94.8%) | 41 hours or more and not more than 48 hours |
| 6.0 mL (15.0 mg) | 5.62 mL (93.7%) | 48 hours (2 days) or more and not more than 3 days |
| 8.0 mL (20.0 mg) | 7.30 mL (91.3%) | 3 days or more and not more than 4 days |

Figure 5:
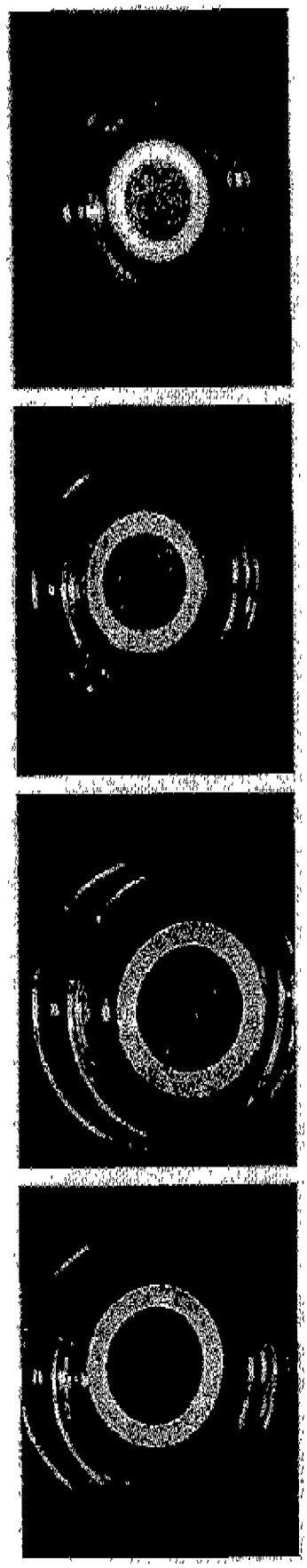
FIG. 5 is a view illustrating a collagen vitrigel membrane accompanied by an amorphous outer peripheral edge.

At the day 1 or day 2 after the vitrification, the dried collagen gel was transferred into a clean bench at room temperature, and it was rehydrated by the addition of 2.0 mL of PBS within the Petri dish and released from the bottom surface and wall surface of the Petri dish, thereby fabricating a ring-shaped nylon membrane support-provided collagen vitrigel membrane. Then, by rinsing with 2.0 mL of PBS several times, a ring-shaped nylon membrane support-provided collagen vitrigel membrane equilibrated with PBS was fabricated. This ring-shaped nylon membrane support-provided collagen vitrigel membrane was entrained with an excessive collagen vitrigel membrane (amorphous outer peripheral edge) originating in the wall surface of the Petri dish in the periphery of the outer circle with a diameter of 33 mm of the ring-shaped nylon membrane support (FIG. 5). Incidentally, at the time of rehydration, even by conducting an tracing operation along the inner wall of the Petri dish by tweezers with sharp tips, it was impossible to cut off the excessive collagen vitrigel membrane in the periphery of the outer circle of this ring-shaped nylon membrane support because the excessive collagen vitrigel membrane protruded from the periphery of the outer circle with a diameter of 33 mm of the ring-shaped nylon membrane support. Accordingly, an operation of cutting out the collagen vitrigel membrane corresponding to the periphery of the outer circle of the ring-shaped nylon membrane support is extremely difficult.

In addition, this ring-shaped nylon membrane support-provided collagen vitrigel membrane contains collagen in an amount of 5.0 mg (derived from 2.0 mL of the collagen sol), 10.0 mg (derived from 4.0 mL of the collagen sol), 15.0 mg (derived from 6.0 mL of the collagen sol), or 20.0 mg (derived from 8.0 mL of the collagen sol) from the left-hand side of FIG. 5. However, in the case of cutting off the excessive collagen vitrigel membrane originating in the wall surface, the precise collagen content cannot be calculated.

In Comparative Example 1, it was also possible to fabricate a ring-shaped nylon membrane support-provided dried collagen vitrigel membrane. However, taking into consideration the difficulty of an operation for the fabrication and the facts that the precise collagen content cannot be calculated and that the drying time of free water within the collagen gel until the vitrification is long, it was confirmed that Comparative Example 1 is not practical.

Example 2

Fabrication of Dried Collagen Vitrigel Membrane (Collagen Amount: 0.52 to 2.1 Mg/Cm$^2$) Adsorbed onto Parafilm Utilizing Parafilm Laid on Substrate and Wall Surface Mold A bottom surface of a hydrophobic polystyrene-made culture Petri dish with a diameter of 60 mm (Falcon #35-1007) was used as a substrate. In addition, an acrylic resin-made mold with a diameter of an outer circle of 39 mm, a diameter of an inner circle of 35 mm, and a height of 10.0 mm was used as a wall surface mold. Parafilm (manufactured by Pechiney Plastic Packaging) was cut in a circle with a diameter of 50 mm and used. Incidentally, each of the wall surface mold and the Parafilm was used after subjecting to a sterilization treatment by spraying 70% ethanol and then wiping it off. Specifically, one sheet of Parafilm cut in a circle with a diameter of 50 mm was laid on the bottom surface of the hydrophobic polystyrene-made culture Petri dish with a diameter of 60 mm, and one wall surface mold was placed thereon, thereby fabricating one container capable of separating the Parafilm laid on the substrate and the wall surface mold from each other.

A collagen gel was fabricated by injecting 2.0 mL, 4.0 mL, 6.0 mL, or 8.0 mL of a 0.25% collagen sol within this container and covering it with a lid of the Petri dish, followed by gelation within a moisturized incubator at 37.0° C. in the presence of 5.0% of $CO_2$ and 95% of air. On that occasion, the injected collagen sol was gelled without being discharged from a gap between the Parafilm laid on the substrate and the wall surface mold.

At the four-hour period, six-hour period, and eight-hour period after transferring into the moisturized incubator at 37.0° C., not only the amount of free water within the collagen gel discharged to the outside of the wall surface mold from the gap between the Parafilm laid on the substrate and the wall surface mold was quantitatively determined, but the discharged free water at the every-hour period was removed. Incidentally, at the two-hour period, the wall surface mold was slightly moved in the vertical direction, thereby unfastened the adhesion between the collagen gel and the wall surface mold. As a result, it was noted that in the collagen gels derived from 6.0 mL and 8.0 mL of the collagen sol, the free water was discharged to the outside of the wall surface mold in a proportion of ⅓ or more at the four-hour period; in the collagen gel derived from 4.0 mL of the collagen sol, the free water was discharged to the outside of the wall surface mold in a proportion of about ⅓ at the six-hour period; and in the collagen gel derived from 2.0 mL of the collagen sol, the free water was discharged to the outside of the wall surface mold in a proportion of about ¼ at the eight-hour period (Table 5).

TABLE 5

| Injection amount of 0.25% collagen sol (collagen amount) | Accumulated discharge amount up to the four-hour period after gelation | Accumulated discharge amount up to the six-hour period after gelation | Accumulated discharge amount up to the eight-hour period after gelation |
|---|---|---|---|
| 2.0 mL (5.0 mg) | 0.23 mL (11.5%) | 0.38 mL (19.0%) | 0.49 mL (24.5%) |
| 4.0 mL (10.0 mg) | 0.62 mL (15.5%) | 1.29 mL (32.3%) | 1.46 mL (36.5%) |
| 6.0 mL (15.0 mg) | 2.30 mL (38.3%) | 2.63 mL (43.8%) | 2.85 mL (47.5%) |
| 8.0 mL (20.0 mg) | 3.20 mL (40.0%) | 3.70 mL (46.3%) | 3.92 mL (49.0%) |

The wall surface mold was removed from the top of the substrate at the eight-hour period. On that occasion, the wall surface mold was in a non-adhered state to the collagen gel, and attachment of the collagen gel to the surroundings such as an inner wall of the wall surface mold removed from Parafilm laid on the substrate, etc. was not observed at all. In addition, at the eight-hour period, the collagen gel was transferred into a clean bench under a condition at 10.0° C. and at a humidity of 40% from the moisturized incubator at 37.0° C. Thereafter, the free water remaining within the collagen gel was completely removed by means of natural drying in a state where the lid of the Petri dish was removed, thereby obtaining a dried collagen gel.

Here, the vitrification starts from the stage at which the free water remaining within the collagen gel has been completely removed. Then, an approximate time required for the natural drying until this vitrification started (until the free water remaining within the collagen gel was completely removed to form a dried collagen gel) was measured. As a result, the time required until the vitrification started was not more than 20 hours in the case of 2.0 mL of the 0.25% collagen gel and 20 hours or more and not more than 41 hours in the case of 4.0 mL, 6.0 mL, and 8.0 mL of the 0.25% collagen gel, respectively (Table 6).

TABLE 6

| Injection amount of 0.25% collagen sol (collagen amount) | Amount of free water remaining within the gel at the eight-hour period after gelation | Time required for drying residual free water |
|---|---|---|
| 2.0 mL (5.0 mg) | 1.51 mL (75.5%) | Not more than 20 hours |
| 4.0 mL (10.0 mg) | 2.54 mL (63.5%) | 20 hours or more and not more than 41 hours |
| 6.0 mL (15.0 mg) | 3.15 mL (52.5%) | 20 hours or more and not more than 41 hours |
| 8.0 mL (20.0 mg) | 4.08 mL (51.0%) | 20 hours or more and not more than 41 hours |

At the day 1 or day 2 after the vitrification, the dried collagen gel was transferred into a clean bench at room temperature, and it was rehydrated by the addition of 5.0 mL of PBS within the Petri dish of the substrate, thereby fabricating a collagen vitrigel membrane in a state where it was adsorbed onto the Parafilm laid on the substrate. Then, by rinsing with 5.0 mL of PBS several times, a collagen vitrigel membrane equilibrated with PBS was fabricated in a state where it was adsorbed onto the Parafilm. This collagen vitrigel membrane reflected the shape of the inner circle (area: 9.6 $cm^2$) with a diameter of 35 mm of the wall surface mold and did not have an amorphous outer peripheral edge.

Figure 6:
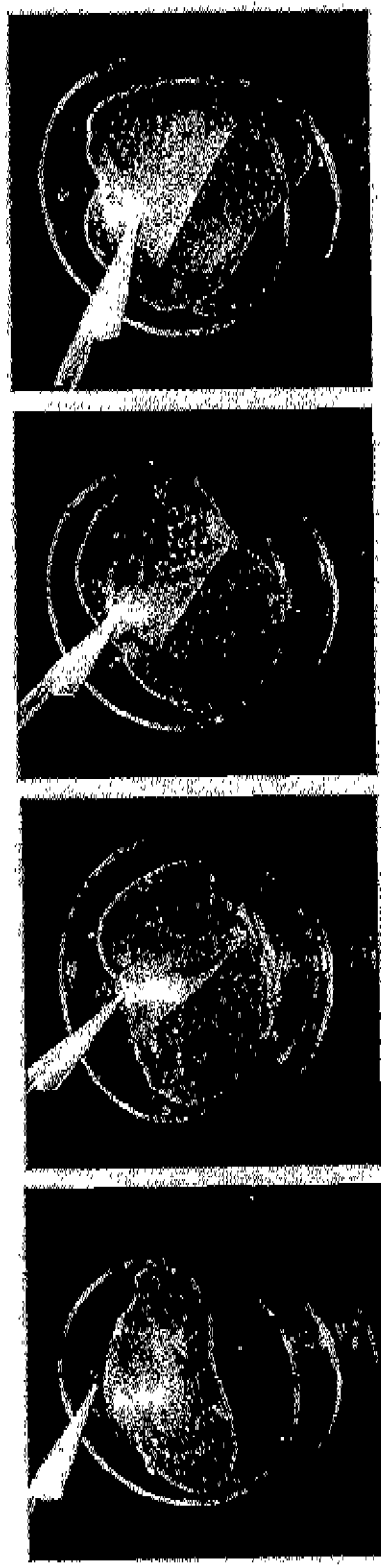
FIG. 6 is a view illustrating a state where a part of a dried collagen vitrigel membrane adsorbed onto Parafilm is easily released from the Parafilm.

Furthermore, this collagen vitrigel membrane in a state where it was adsorbed onto the Parafilm was transferred into a hydrophobic polystyrene-made culture Petri dish with a diameter of 60 mm (Falcon #35-1007) and allowed to stand for complete drying for from about 1 to 2 days within a clean bench under a condition at 10.0° C. and at a humidity of 40% in a state where a lid thereof was removed. Thereafter, each of the Petri dishes was transferred into a clean bench at room temperature and covered it with a lid. Thereafter, the Petri dish was sterilely stored and maintained at room temperature to allow the vitrification to proceed, thereby fabricating a dried collagen vitrigel membrane in a state where it was adsorbed onto the Parafilm. This dried collagen vitrigel membrane in a state where it was adsorbed onto the Parafilm could be easily cut in a desired fine shape by using scissors, a surgical knife, or the like. In addition, it was also possible to release the dried collagen vitrigel membrane from the Parafilm (FIG. 6).

The collagen vitrigel membrane fabricated in this step contains collagen in an amount of 5.0 mg (derived from 2.0 mL of the collagen sol), 10.0 mg (derived from 4.0 mL of the collagen sol), 15.0 mg (derived from 6.0 mL of the collagen sol), or 20.0 mg (derived from 8.0 mL of the collagen sol). In addition, the dried collagen vitrigel membrane fabricated in this step contains collagen in an amount of 0.52 mg (derived from 2.0 mL of the collagen sol), 1.0 mg (derived from 4.0 mL of the collagen sol), 1.6 mg (derived from 6.0 mL of the collagen sol), or 2.1 mg (derived from 8.0 mL of the collagen sol) per unit area (1.0 $cm^2$) from the left-hand side of FIG. 6.

Figure 7:
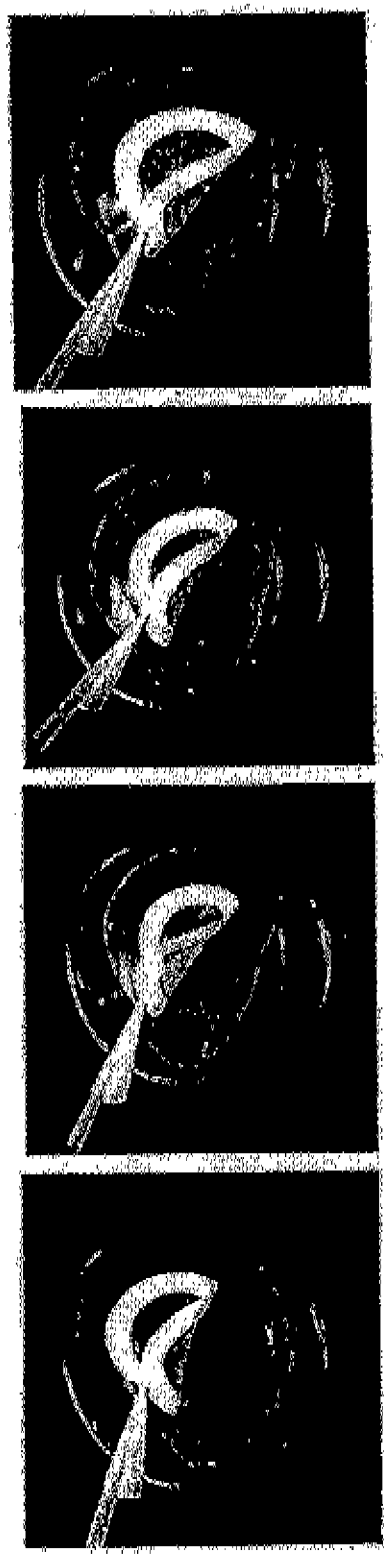
FIG. 7 is a view illustrating a state where a part of a ring-shaped nylon membrane support-provided collagen vitrigel membrane adsorbed onto Parafilm is easily released from the Parafilm.

Incidentally, in the foregoing steps, if a ring-shaped nylon membrane is inserted into the collagen sol, a ring-shaped nylon membrane support-provided dried collagen vitrigel membrane can be fabricated in a state where it is adsorbed onto the Parafilm (FIG. 7). In addition, if the bottom planar surface shape and height of the wall surface mold are modified, a dried collagen vitrigel membrane having arbitrary shape and thickness can be fabricated in a state where it is adsorbed onto the Parafilm.

Example 3

Quick Mass-Production Method of Ring-Shaped Nylon Membrane Support-Provided Dried Collagen Vitrigel Membrane Utilizing Substrate and Wall Surface Mold A bottom surface of a hydrophobic polystyrene-made culture Petri dish of 100 mm×100 mm (Falcon #35-1112) was used as a substrate. In addition, four acrylic resin-made molds with a diameter of an outer circle of 38 mm, a diameter of an inner circle of 34 mm, and a height of 10.0 mm were used as a wall surface mold. In addition, the wall surface molds were used after subjecting to a sterilization treatment by spraying 70% ethanol and then wiping it off.

Figure 8:
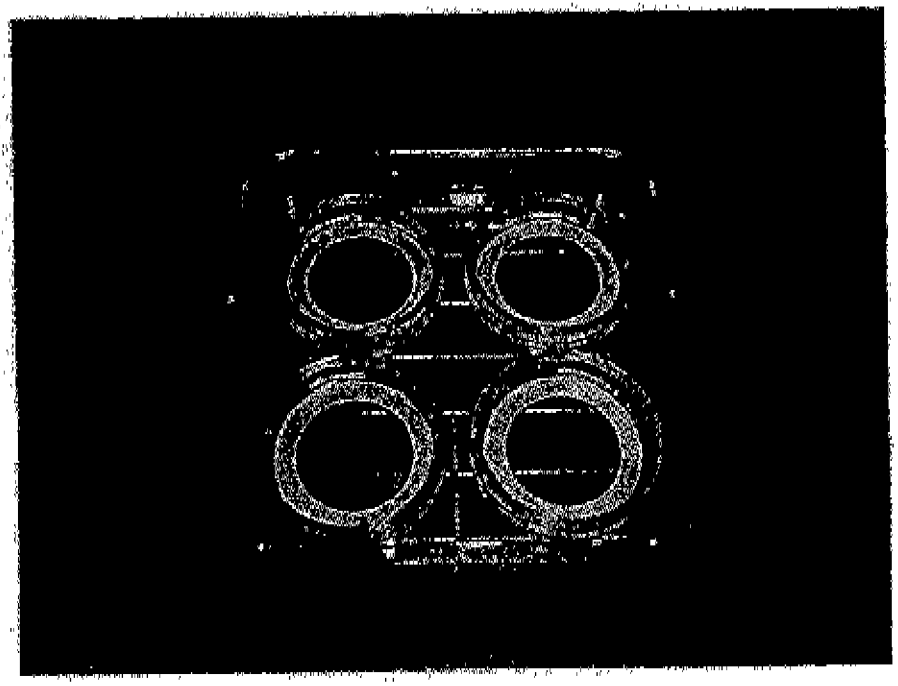
FIG. 8 is a view illustrating a state where four wall surface molds are placed on one substrate, and a collagen sol is injected into the inside of each of the wall surface molds.

Specifically, four wall surface molds were placed on one substrate, thereby fabricating four containers capable of separating the substrate and the wall surface mold from each other. One sheet of a ring-shaped nylon membrane support was inserted into each of the containers, 2.0 mL of a 0.25% collagen sol was injected, and the substrate was covered with a lid of the Petri dish, followed by gelation within a moisturized incubator at 37.0° C. in the presence of 5.0% of $CO_2$ and 95% of air, thereby fabricating four collagen gels on one substrate. On that occasion, the injected collagen sol was gelled without being discharged from a gap between the substrate and the wall surface mold (FIG. 8).

Figure 9:
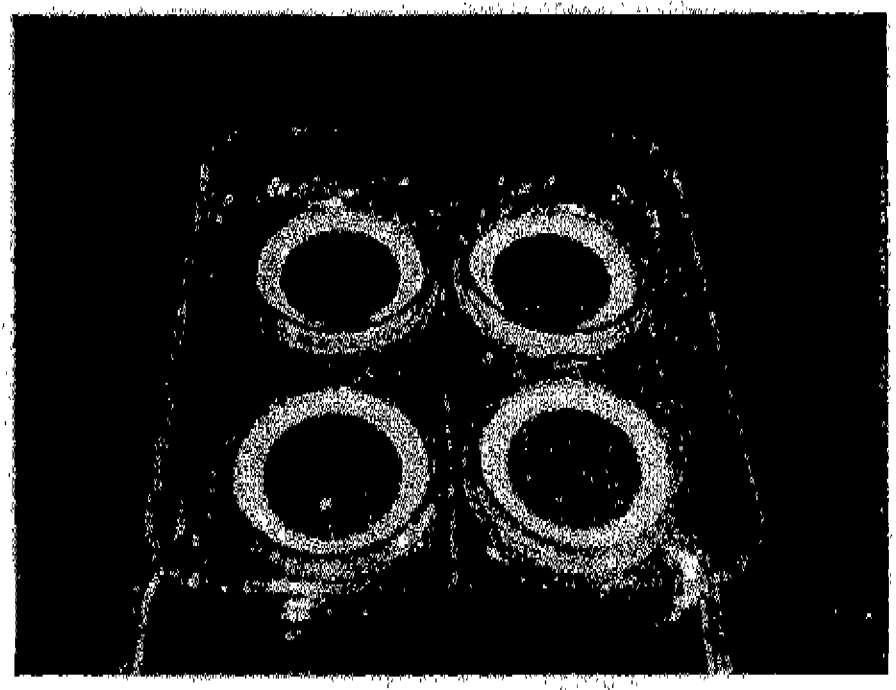
FIG. 9 is a view illustrating a state where in the form of FIG. 8, each of the wall surface molds is slightly moved in the vertical direction, thereby unfastened the adhesion between the collagen gel and the wall surface mold.
Figure 10:
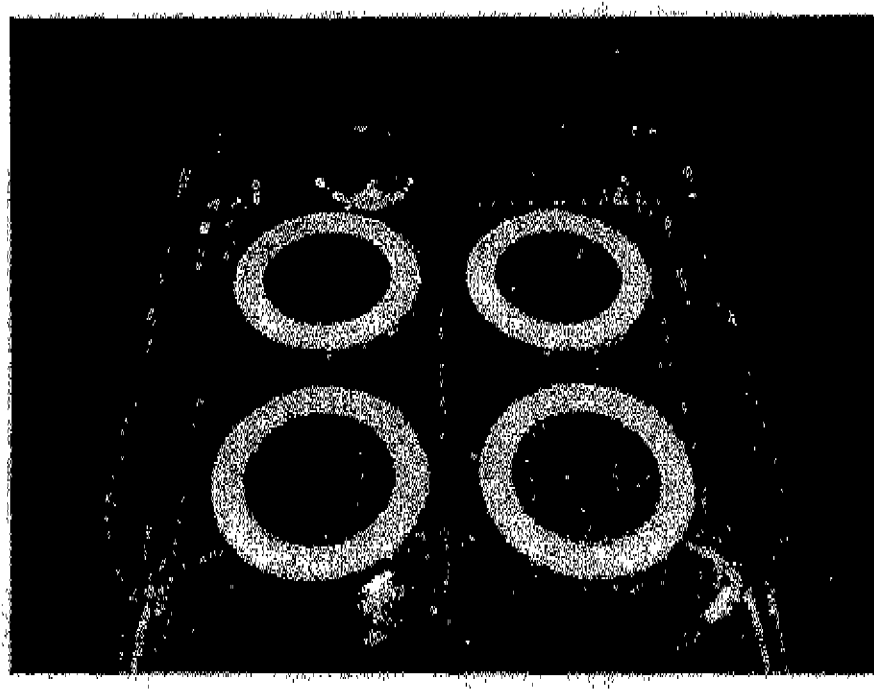
FIG. 10 is a view illustrating a state where in the form of FIG. 8, each of the wall surface molds is removed from the top of the substrate.

In addition, at the two-hour period after transferring into the moisturized incubator at 37.0° C., the wall surface mold was slightly moved in the vertical direction, thereby unfastened the adhesion between the collagen gel and the wall surface mold (FIG. 9). Thereafter, free water was discharged to the outside of the wall surface mold in a proportion of about ⅓ at the four-hour period, and therefore, the wall surface mold was removed from the top of the substrate (FIG. 10). After removing the discharged free water, the collagen gel was transferred into a clean bench under a condition at 10.0° C. and at a humidity of 40%. Thereafter, the free water remaining within the collagen gel was completely removed by means of natural drying in a state where the lid of the Petri dish was removed, thereby obtaining a dried collagen gel.

Here, the vitrification starts from the stage at which the free water remaining within the collagen gel has been completely removed. Then, the natural drying until this vitrification started (until the free water remaining within the collagen gel was completely removed to form a dried collagen gel) was completed within one day. At the day 1 or day 2 after the vitrification, the dried collagen gel was transferred into a clean bench at room temperature, and it was rehydrated by the addition of 20 mL of PBS within the Petri dish of the substrate and released from the substrate, thereby fabricating four ring-shaped nylon membrane support-provided collagen vitrigel membranes at the same time. Subsequently, the same operations as those in Example 1 were followed to fabricate four ring-shaped nylon membrane support-provided dried collagen vitrigel membranes containing 0.55 mg of collagen per unit area (1.0 $cm^2$) at the same time.

Incidentally, in the foregoing step, if the ring-shaped nylon membrane is not inserted, four ring-shaped nylon membrane support-free dried collagen vitrigel membranes can be fabricated at the same time. In addition, in the foregoing step, Parafilm is laid on the substrate and used in the same manner as that in Example 2, four dried collagen vitrigel membranes adsorbed onto the Parafilm can be fabricated at the same time.

Example 4

Fabrication of Ring-Shaped Nylon Membrane Support-Provided Dried Collagen Vitrigel Membrane (Collagen Amount: 2.7 to 11.0 Mg/Cm$^2$) Utilizing Substrate and Wall Surface Mold In order to make it possible to inject a 0.25% collagen sol in an amount of from 10.0 mL to 40.0 mL into the container of Example 1, which is capable of separating the substrate and the wall surface mold from each other, a wall surface mold having a height higher than that of the wall surface mold used in Example 1 was fabricated, and the same experiments as those in Example 1 were conducted.

Specifically, a wall surface mold made of an acrylic resin and having a diameter of the outer circle of 38 mm, a diameter of an inner circle of 34 mm, and a height of 30.0 mm or 60.0 mm was fabricated. As a substrate, a bottom surface of a hydrophobic polystyrene-made culture Petri dish with a diameter of 60 mm (Falcon #35-1007) was used for the wall surface mold having a height of 30.0 mm, and a bottom surface of a hydrophobic polystyrene-made culture Petri dish of 100 mm×100 mm (Falcon #35-1112) was used for the wall surface mold having a height of 60.0 mm. In each of these cases, one wall surface mold was placed on one substrate, thereby fabricating one container capable of separating the substrate and the wall surface mold from each other, and one sheet of a ring-shaped nylon membrane support was inserted into each of the containers. Immediately thereafter, a 0.25% collagen sol in an amount of 10.0 mL, 12.0 mL, 16.0 mL, or 20.0 mL was injected into the container having a wall surface mold having a height of 30.0 mm, and a 0.25% collagen sol in an amount of 24.0 mL, 28.0 mL, 32.0 mL, 36.0 mL, or 40.0 mL was injected into the container having a wall surface mold having a height of 60.0 mm. After covering the substrate by a lid of each of the Petri dishes, gelation was conducted within a moisturized incubator at 37.0° C. in the presence of 5.0% of $CO_2$ and 95% of air, thereby fabricating a collagen gel. On that occasion, the injected collagen sol was gelled without being discharged from a gap between the substrate and the wall surface mold. At the two-hour period, four-hour period, six-hour period, and eight-hour period after transferring into the moisturized incubator at 37.0° C., not only the amount of free water within the collagen gel discharged to the outside of the wall surface mold from the gap between the substrate and the wall surface mold was quantitatively determined, but the discharged free water at the every-hour period was removed. Incidentally, at the two-hour period, the wall surface mold was slightly moved in the vertical direction, thereby unfastened the adhesion between the collagen gel and the wall surface mold.

Incidentally, the wall surface mold was removed from the top of the substrate at the eight-hour period. On that occasion, the wall surface mold was in a non-adhered state to the collagen gel, and attachment of the collagen gel to the surroundings such as an inner wall of the wall surface mold removed from the substrate, etc. was not observed at all. In addition, at the eight-hour period, the collagen gel was transferred into a clean bench under a condition at 10.0° C. and at a humidity of 40% from the moisturized incubator at 37.0° C. Thereafter, the free water discharged in a state where the lid of the Petri dish was removed, was discharged. Here, with respect to the hydrophobic polystyrene-made culture Petri dish with a diameter of 60 mm, in which the 0.25% collagen sol in an amount of from 10.0 mL to 20.0 mL was injected into the wall surface mold having a height of 30.0 mm, the free water remaining within the collagen gel was completely removed by means of natural drying, thereby obtaining a vitrified dried collagen gel. In addition, with respect to the hydrophobic polystyrene-made culture Petri dish of 100 mm×100 mm, in which the 0.25% collagen sol in an amount of from 24.0 mL to 40.0 mL was injected into the wall surface mold having a height of 60.0 mm, since the amount of the discharged free water was large, 1.5 hours after transferring into the clean bench under a condition at 10.0° C. and at a humidity of 40% (at the 9.5-hour period after the gel fabrication), the amount of free water discharged to the outside of the collagen gel was also quantitatively determined, and after removing that free water, the free water remaining within the collagen gel was completely removed by means of natural drying, thereby obtaining a vitrified dried collagen gel.

As a result, it was noted that with respect to the collagen gels of 10.0 mL and 12.0 mL, the free water was discharged to the outside of the wall surface mold in a proportion of about ½ at the eight-hour period, and with respect to the collagen gels of 16.0 mL and 20.0 mL, the free water was discharged to the outside of the wall surface mold in a proportion of ⅔ or more at the eight-hour period (Table 7).

TABLE 7

| Injection amount of 0.25% collagen sol (collagen amount) | Accumulated discharge amount up to the two-hour period after gelation | Accumulated discharge amount up to the four-hour period after gelation | Accumulated discharge amount up to the six-hour period after gelation | Accumulated discharge amount up to the eight-hour period after gelation |
|---|---|---|---|---|
| 10.0 ml (25.0 mg) | 0.79 ml (7.90%) | 2.70 ml (27.0%) | 4.15 ml (41.5%) | 4.79 ml (47.9%) |
| 12.0 ml (30.0 mg) | 1.19 ml (9.92%) | 3.27 ml (27.3%) | 4.87 ml (40.6%) | 5.84 ml (48.7%) |
| 16.0 ml (40.0 mg) | 5.66 ml (35.4%) | 7.51 ml (46.9%) | 9.46 ml (59.1%) | 11.2 ml (70.0%) |
| 20.0 ml (50.0 mg) | 6.30 ml (31.5%) | 9.64 ml (48.2%) | 12.8 ml (64.0%) | 14.2 ml (71.0%) |

Furthermore, it was noted that with respect to the collagen gels of from 24.0 mL to 40.0 mL, the free water was discharged to the outside of the wall surface mold in a proportion of ½ or more at the eight-hour period and about ⅔ at the 9.5-hour period, respectively (Table 8).

TABLE 8

| Injection amount of 0.25% collagen sol (collagen amount) | Amount of free water remainingwithin the gel at the eight-hour period after gelation | Time required for drying residual free water |
|---|---|---|
| 10.0 ml (25.0 mg) | 5.21 ml (52.1%) | 21 hours or more and not more than 37 hours |
| 12.0 ml (30.0 mg) | 6.16 ml (51.3%) | 40 hours or more and not more than 43 hours |
| 16.0 ml (40.0 mg) | 4.80 ml (30.0%) | 37 hours or more and not more than 40 hours |

TABLE 8-continued

| Injection amount of 0.25% collagen sol (collagen amount) | Amount of free water remaining within the gel at the eight-hour period after gelation | Time required for drying residual free water |
|---|---|---|
| 20.0 ml (50.0 mg) | 5.84 ml (29.2%) | 37 hours or more and not more than 40 hours |

Incidentally, the vitrification starts from the stage at which the free water remaining within the collagen gel has been completely removed. Then, an approximate time required for the natural drying until this vitrification started was measured. As a result, the time required until the vitrification started (until the free water remaining within the collagen gel was completely removed to form a dried collagen gel) was 21 hours or more and not more than 37 hours in the case of 10.0 mL of the 0.25% collagen gel, 40 hours or more and not more than 43 hours in the case of 12.0 mL of the 0.25% collagen gel, and 37 hours or more and not more than 40 hours in the case of 16.0 mL and 20.0 mL of the 0.25% collagen gel, respectively (Table 9).

TABLE 9

| Injection amount of 0.25% collagen sol (collagen amount) | Accumulated discharge amount up to the two-hour period after gelation | Accumulated discharge amount up to the four-hour period after gelation | Accumulated discharge amount up to the six-hour period after gelation | Accumulated discharge amount up to the eight-hour period after gelation | Accumulated discharge amount up to the 9.5-hour period after gelation |
|---|---|---|---|---|---|
| 24.0 ml (60.0 mg) | 5.82 ml (24.3%) | 7.59 ml (31.6%) | 9.80 ml (40.8%) | 12.3 ml (51.3%) | 15.2 ml (63.3%) |
| 28.0 ml (70.0 mg) | 7.66 ml (27.4%) | 11.1 ml (39.6%) | 13.7 ml (48.9%) | 16.5 ml (58.9%) | 18.1 ml (64.6%) |
| 32.0 ml (80.0 mg) | 8.38 ml (26.2%) | 12.7 ml (39.7%) | 16.2 ml (50.6%) | 20.5 ml (64.1%) | 21.3 ml (66.6%) |
| 36.0 ml (90.0 mg) | 8.60 ml (23.9%) | 11.5 ml (31.9%) | 16.7 ml (46.4%) | 21.5 ml (59.7%) | 23.2 ml (64.4%) |
| 40.0 ml (100 mg) | 7.30 ml (18.3%) | 10.8 ml (27.0%) | 19.5 ml (48.8%) | 26.8 ml (67.0%) | 27.3 ml (68.3%) |

Furthermore, the time required until the vitrification started was not more than 47 hours in the case of 24.0 mL and 32.0 mL of the 0.25% collagen gel, 47 hours or more and not more than 51 hours in the case of 28.0 mL of the 0.25% collagen gel, 51 hours or more and not more than 62 hours in the case of 36.0 mL of the 0.25% collagen gel, and 47 hours or more and not more than 51 hours in the case of 40.0 mL of the 0.25% collagen gel, respectively (Table 10).

TABLE 10

| Injection amount of 0.25% collagen sol (collagen amount) | Amount of free water remaining within the gel at the 9.5-hour period after gelation | Time required for drying residual free water |
|---|---|---|
| 24.0 ml (60.0 mg) | 8.80 ml (36.7%) | Not more than 47 hours |
| 28.0 ml (70.0 mg) | 9.94 ml (35.5%) | 47 hours or more and not more than 51 hours |
| 32.0 ml (80.0 mg) | 10.7 ml (33.4%) | Not more than 47 hours |
| 36.0 ml (90.0 mg) | 12.8 ml (35.6%) | 51 hours or more and not more than 62 hours |
| 40.0 ml (100 mg) | 12.7 ml (31.8%) | 47 hours or more and not more than 51 hours |

Namely, in the 0.25% collagen gels in an amount of from 10.0 mL to 40.0 mL, the time required for the natural drying was not more than 62 hours even at maximum, and it was noted that a vitrified dried collagen gel was obtained within 3 days after injecting the collagen sol into a container composed of the substrate and the wall surface mold.

At the day 1 or day 2 after the vitrification, the dried collagen gel was transferred into a clean bench at room temperature, and it was rehydrated by the addition of 5.0 mL of PBS within the Petri dish in the case where the Petri dish of the substrate was the hydrophobic polystyrene-made culture Petri dish with a diameter of 60 mm, or 20.0 mL of PBS within the Petri dish in the case where the Petri dish of the substrate was the hydrophobic polystyrene-made culture Petri dish of 100 mm×100 mm, and released from the substrate, thereby fabricating a ring-shaped nylon membrane support-provided collagen vitrigel membrane. Then, by rinsing with PBS several times, a ring-shaped nylon membrane support-provided collagen vitrigel membrane equilibrated with PBS was fabricated. This ring-shaped nylon membrane support-provided collagen vitrigel membrane reflected the shape of the inner circle (area: 9.1 cm$^2$) with a diameter of 34 mm of the wall surface mold and imbedded the periphery of the outer circle with a diameter of 33 mm of the ring-shaped nylon membrane support with a slight clearance therein.

The collagen vitrigel membrane fabricated in this step contains collagen in an amount of 25.0 mg (derived from 10.0 mL of the collagen sol), 30.0 mg (derived from 12.0 mL of the collagen sol), 40.0 mg (derived from 16.0 mL of the collagen sol), 50.0 mg (derived from 20.0 mL of the collagen sol), 60.0 mg (derived from 24.0 mL of the collagen sol), 70.0 mg (derived from 28.0 mL of the collagen sol), 80.0 mg (derived from 28.0 mL of the collagen sol), 90.0 mg (derived from 36.0 mL of the collagen sol), or 100.0 mg (derived from 40.0 mL of the collagen sol).

Furthermore, this ring-shaped nylon membrane support-provided collagen vitrigel membrane was transferred into a hydrophilic polystyrene-made culture Petri dish with a diameter of 35 mm (Falcon #35-3001) and a hydrophobic polystyrene-made culture Petri dish with a diameter of 60 mm, in which Parafilm (manufactured by Pechiney Plastic Packaging) was laid on the bottom surface thereof (Falcon #35-1007), respectively and allowed to stand for complete drying for about 1 to 2 days within a clean bench under a condition at 10.0° C. and at a humidity of 40% in a state where a lid thereof was removed. Thereafter, each of the Petri dishes was transferred into a clean bench at room temperature and covered with a lid. Thereafter, each of the Petri dishes was sterilely stored and maintained at room temperature to allow the vitrification to proceed, thereby fabricating respective ring-shaped nylon membrane support-provided dried collagen vitrigel membranes.

The dried collagen vitrigel membrane fabricated in this step contains collagen in an amount of 2.7 mg (derived from 10.0 mL of the collagen sol), 3.3 mg (derived from 12.0 mL of the collagen sol), 4.4 mg (derived from 16.0 mL of the collagen sol), 5.5 mg (derived from 20.0 mL of the collagen sol), 6.6 mg (derived from 24.0 mL of the collagen sol), 7.7 mg (derived from 28.0 mL of the collagen sol), 8.8 mg (derived from 32.0 mL of the collagen sol), 9.9 mg (derived from 36.0 mL of the collagen sol), or 11.0 mg (derived from 40.0 mL of the collagen sol) per unit area (1.0 cm$^2$).

Comparative Example 2

Fabrication of Ring-Shaped Nylon Membrane Support-Provided Dried Collagen Vitrigel Membrane Utilizing Conventional Culture Petri Dish Experiments were conducted in the same manner as that in Example 4, except that a conventional hydrophobic polystyrene-made culture Petri dish (Falcon #35-1008) was used instead of utilizing the wall surface mold capable of be separated from the substrate in Example 4.

Specifically, one sheet of a ring-shaped nylon membrane support was inserted into this culture Petri dish, and immediately thereafter, it was attempted to inject a 0.25% collagen sol in an amount of from 10.0 mL to 40.0 mL. However, it was noted that when 10.0 mL of the 0.25% collagen sol was injected, the injected collagen sol swelled up in a dome state above the height of the Petri dish, so that the Petri dish could not be covered with a lid; and that when the 0.25% collagen sol in an amount of 12.0 mL or more was injected, the collagen sol overflowed exceeding a tolerable amount of the Petri dish. Namely, it was noted that in the conventional hydrophobic polystyrene-made culture Petri dish with a diameter of 35 mm, a collagen sol in an amount of 10.0 mL or more could not be fabricated.

Example 5

Measurement of Thickness of Ring-Shaped Nylon Membrane Support-Free Collagen Vitrigel Membrane Fabricated Utilizing Substrate and Wall Surface Mold In Example 4, by using a wall surface mold made of an acrylic resin and having a diameter of an outer circle of 39 mm, a diameter of an inner circle of 35 mm, and a height of 60.0 mm and, as a substrate, a bottom surface of a hydrophobic polystyrene-made culture Petri dish of 100 mm×100 mm (Falcon #35-1112) and placing one wall surface mold on one substrate, one container capable of separating the substrate and the wall surface mold from each other was fabricated. A 0.25% collagen sol in an amount of 20.0 mL, 24.0 mL, 28.0 mL, 32.0 mL, 36.0 mL, or 40.0 mL was injected into each of the containers without inserting a ring-shaped nylon membrane and gelled within a moisturized incubator at 37.0° C. in the presence of 5.0% of $CO_2$ and 95% of air, and free water within the collagen gel was discharged to the outside of the wall surface mold from a gap between the substrate and the wall surface mold and removed over 8 hours. Thereafter, each of the collagen gels was transferred into a clean bench under a condition at 10.0° C. and at a humidity of 40%, and 1.5 hours later (at the 9.5-hour period after the gel fabrication), with respect to each of the collagen gels, free water discharged to the outside was removed. Furthermore, the free water remaining within each of the collagen gels was completely removed by means of natural drying over 3 days, thereby obtaining a vitrified dried collagen gel. At the day 1 after the vitrification, each of the dried collagen gels was transferred into a clean bench at room temperature, and it was rehydrated by the addition of 20.0 mL of PBS within the Petri dish of the substrate and released from the substrate, thereby fabricating a collagen vitrigel membrane. Then, by rinsing with PBS several times, a collagen vitrigel membrane equilibrated with PBS was fabricated. Each of the collagen vitrigel membranes reflected the shape of the inner circle (area: 9.6 cm$^2$) with a diameter of 35 mm of the wall surface mold and did not have an amorphous outer peripheral edge.

Each of the thus fabricated ring-shaped nylon membrane support-free collagen vitrigel membranes was measured for the thickness. Specifically, one sheet of the collagen vitrigel membrane was interposed between two slide glasses (Matsunami #S-0317), installed in a micrometer (Mitutoyo's digimatic micrometer #MDC-25M), and measured. As a result, the collagen vitrigel membrane containing 50.0 mg of collagen (derived from 20.0 mL of the collagen sol) was 428±148.1 μm (measured three times); the collagen vitrigel membrane containing 60.0 mg of collagen (derived from 24.0 mL of the collagen sol) was 635±21.4 μm (measured three times); the collagen vitrigel membrane containing 70.0 mg of collagen (derived from 28.0 mL of the collagen sol) was 714±34.6 μm (measured three times); the collagen vitrigel membrane containing 80.0 mg of collagen (derived from 32.0 mL of the collagen sol) was 774±29.9 μm (measured three times); the collagen vitrigel membrane containing 90.0 mg of collagen (derived from 36.0 mL of the collagen sol) was 934±22.2 μm (measured three times); and the collagen vitrigel membrane containing 100.0 mg of collagen (derived from 40.0 mL of the collagen sol) was 1,073±58.5 μm (measured three times).

Example 6

Fabrication of Laminate Having Dried Collagen Vitrigel Membranes Superposed Therein A bottom surface of a hydrophobic polystyrene-made culture Petri dish of 100 mm×100 mm was used as a substrate, and four acrylic resin-made molds with a diameter of an outer circle of 38 mm, a diameter of an inner circle of 34 mm, and a height of 30 mm were used as a wall surface mold. Four wall surface molds were placed on one substrate, thereby fabricating four containers capable of separating the substrate and the wall surface mold from each other. One sheet of a ring-shaped nylon membrane support was inserted into each of the containers, 2.0 mL of a 0.25% collagen sol was injected, and the substrate was covered with a lid of the Petri dish, followed by gelation within a moisturized incubator at 37.0° C. in the presence of 5.0% of $CO_2$ and 95% of air, thereby fabricating four collagen gels on one substrate.

At the two-hour period after transferring into the moisturized incubator at 37.0° C., the wall surface mold was slightly moved in the vertical direction, thereby unfastened the adhesion between the collagen gel and the wall surface mold. Thereafter, free water was discharged to the outside of the wall surface mold in a proportion of about ¼ at the four- to six-hour period, and therefore, the wall surface mold was removed from the substrate. After removing the discharged free water, the collagen gel was transferred into a clean bench under a condition at 10.0° C. and at a humidity of 40%. Thereafter, the free water remaining within the collagen gel was completely removed by means of natural drying for 2 days in a state where the lid of the Petri dish was removed, thereby obtaining a dried collagen gel.

This vitrified dried collagen gel was rehydrated by the addition of 10 mL of a cell culture medium (having the same composition as that in Example 1) within the Petri dish of the substrate and released from the substrate, thereby fabricating four ring-shaped nylon membrane support-provided collagen vitrigel membranes.

Furthermore, four wall surface molds were placed on one substrate, thereby again fabricating four containers capable of separating the substrate and the wall surface mold from each other. Then, the cell culture medium of the ring-shaped nylon membrane support-provided collagen vitrigel membrane fabricated by the foregoing method was removed, and this ring-shaped nylon membrane support-provided collagen vitrigel membrane was inserted one by one into each of the containers.

Subsequently, 2.0 mL of a 0.25% collagen sol was injected into each of the containers in the same manner as described above, and a series of operations including gelation, discharge of free water within the collagen gel, complete removal of free water under a condition at 10.0° C. and at a humidity of 40%, and rehydration with 10 mL of a cell culture medium were repeated twice (the final rehydration was conducted using 20 mL of PBS in place of 10 mL of the cell culture medium), followed by rinsing with PBS several times, thereby achieving equilibration with PBS. According to this, four laminates having the ring-shaped nylon membrane support and having the collagen vitrigel membranes superposed therein (derived from three layers of 2.0 mL of the 0.25% collagen sol) could be fabricated.

This laminate having collagen vitrigel membranes superposed therein contained 15.0 mg of collagen and reflected the shape of the inner circle with a diameter of 34 mm of the wall surface mold.

In addition, the laminate having collagen vitrigel membranes superposed therein (derived from three layers of 2.0 mL of the 0.25% collagen sol) was installed in a micrometer and measured for the thickness. As a result, the thickness was 65±2 μm (average value after the measurement of three times). This was equal to the thickness of 69±5 μm (average value after the measurement of three times) of the collagen vitrigel fabricated by the method of Example 3 (derived from 6.0 mL of the 0.25% collagen sol).

Furthermore, this laminate of collagen vitrigel membranes was transferred into a hydrophobic polystyrene-made culture Petri dish of 100 mm×100 mm, in which Parafilm was laid on the bottom surface thereof, and allowed to stand for complete drying within the collagen gel for about one day within a clean bench under a condition at 10.0° C. and at a humidity of 40% in a state where a lid thereof was removed. Thereafter, the Petri dish was covered with a lid and sterilely stored and maintained at room temperature to allow the vitrification to proceed, thereby fabricating a laminate having dried collagen vitrigel membranes superposed therein.

Then, the laminate of dried collagen vitrigel membrane fabricated in this step contained 1.65 mg of collagen per unit area (1.0 cm$^2$).

Example 7

Fabrication of Laminate Having Separately Fabricated Dried Collagen Vitrigel Membranes Superposed Therein A bottom surface of a hydrophobic polystyrene-made culture Petri dish of 100 mm×100 mm was used as a substrate, and four acrylic resin-made molds with a diameter of an outer circle of 38 mm, a diameter of an inner circle of 34 mm, and a height of 30 mm were used as a wall surface mold. Four wall surface molds were placed on one substrate, thereby fabricating four containers capable of separating the substrate and the wall surface mold from each other. After injecting 2.0 mL of a 0.25% collagen sol into each of the containers, a dried collagen vitrigel membrane fabricated according to Example 4 (derived from 10.0 mL of the 0.25% collagen sol) was inserted, into which was then again injected 2.0 mL of a 0.25% collagen sol. Furthermore, a dried collagen vitrigel membrane fabricated according to Example 4 (derived from 10.0 mL of the 0.25% collagen sol) was inserted, and finally, 2.0 mL of a 0.25% collagen sol was injected. The substrate was covered with a lid of the Petri dish, followed by gelation within a moisturized incubator at 37.0° C. in the presence of 5.0% of $CO_2$ and 95% of air, thereby fabricating four collagen gels on one substrate.

At the two-hour period after transferring into the moisturized incubator at 37.0° C., the wall surface mold was slightly moved in the vertical direction, thereby unfastened the adhesion between the collagen gel and the wall surface mold. Thereafter, free water was discharged to the outside of the wall surface mold in a proportion of about ⅓ at the three-hour period, and therefore, the wall surface mold was removed from the substrate. After removing the discharged free water, the collagen gel was transferred into a clean bench under a condition at 10.0° C. and at a humidity of 40%. Thereafter, the free water remaining within the collagen gel was completely removed by means of natural drying for 2 days in a state where the lid of the Petri dish was removed, thereby obtaining a laminate having dried collagen gels superposed therein. This laminate of vitrified dried collagen gels was rehydrated by the addition of 20 mL of PBS within the Petri dish of the substrate and released from the substrate, thereby fabricating four laminates of collagen vitrigel membranes. Then, by rinsing with PBS several times, four laminates of collagen vitrigel membranes equilibrated with PBS were fabricated. This laminate of collagen vitrigel membranes contained 65.0 mg of collagen and reflected the shape of the inner circle with a diameter of 34 mm of the wall surface mold.

In addition, the thus fabricated laminate of collagen vitrigel membranes (derived from the 0.25% collagen sol of (2.0 mL+10.0 mL+2.0 mL+10.0 mL+2.0 mL (26 mL in total)) was measured for the thickness according to the method of Example 6. As a result, the thickness was 336±20 μm (average value after the measurement of three times).

Furthermore, this laminate of collagen vitrigel membranes was transferred into a hydrophobic polystyrene-made culture Petri dish of 100 mm×100 mm, in which Parafilm was laid on the bottom surface thereof, and allowed to stand for complete drying within the collagen gel for about one day within a clean bench under a condition at 10.0° C. and at a humidity of 40% in a state where a lid thereof was removed. Thereafter, the Petri dish was covered with a lid and sterilely stored and maintained at room temperature to allow the vitrification to proceed, thereby fabricating a laminate of dried collagen vitrigel membranes.

The laminate of dried collagen vitrigel membranes fabricated in this step contains 7.15 mg of collagen per unit area (1.0 cm$^2$).

Example 8

Fabrication of Dried Vitrigel Membrane Containing FITC-Labeled Goat Anti-Mouse Antibody A bottom surface of a hydrophobic polystyrene-made culture Petri dish of 100 mm×100 mm was used as a substrate, and four acrylic resin-made molds with a diameter of an outer circle of 38 mm, a diameter of an inner circle of 34 mm, and a height of 30 mm were used as a wall surface mold. Four wall surface molds were placed on one substrate, thereby fabricating four containers capable of separating the substrate and the wall surface mold from each other. One sheet of a ring-shaped nylon membrane support was inserted into each of the containers, 2.0 mL of a 0.25% collagen sol was injected, and the substrate was covered with a lid of the Petri dish, followed by gelation within a moisturized incubator at 37.0° C. in the presence of 5.0% of $CO_2$ and 95% of air, thereby fabricating four collagen gels on one substrate.

At the two-hour period after transferring into the moisturized incubator at 37.0° C., the wall surface mold was slightly moved in the vertical direction, thereby unfastened the adhesion between the collagen gel and the wall surface mold. Thereafter, free water was discharged to the outside of the wall surface mold in a proportion of about ⅓ at the four- to six-hour period, and therefore, the wall surface mold was removed from the substrate. After removing the discharged free water, the collagen gel was transferred into a clean bench under a condition at 10.0° C. and at a humidity of 40%. Thereafter, the free water remaining within the collagen gel was completely removed by means of natural drying for 2 days in a state where the lid of the Petri dish was removed, thereby obtaining a dried collagen gel.

This vitrified dried collagen gel was rehydrated by the addition of 10 mL of a cell culture medium (having the same composition as that in Example 1) within the Petri dish of the substrate and released from the substrate, thereby fabricating four ring-shaped nylon membrane support-provided collagen vitrigel membranes. After removing the cell culture medium, four wall surface molds were placed on one substrate such that one sheet of this ring-shaped nylon membrane support-provided collagen vitrigel membrane was inserted into each of the containers, thereby again fabricating four containers capable of separating the substrate and wall surface mold from each other.

Furthermore, 2.0 mL of a 0.25% collagen sol containing a 1% FITC-labeled goat anti-mouse IgG antibody solution was injected into each of the containers, and a series of operations including gelation, discharge of free water within the collagen gel, complete removal of free water under a condition at 10.0° C. and at a humidity of 40%, and rehydration with 10 mL of a cell culture medium were conducted. According to this, the ring-shaped nylon membrane support-provided collagen vitrigel membrane and the collagen vitrigel membrane containing an FITC-labeled goat anti-mouse IgG antibody were superposed with each other.

Furthermore, four wall surface molds were placed on one substrate, thereby again fabricating four containers capable of separating the substrate and the wall surface mold from each other. After removing the culture medium of the superposed collagen vitrigel membrane, one sheet of the resulting membrane was inserted into each of the containers.

Subsequently, 2.0 mL of a 0.25% collagen sol was injected into each of the containers, and a series of operations including gelation, discharge of free water within the collagen gel, complete removal of free water under a condition at 10.0° C. and at a humidity of 40%, and rehydration with 20 mL of PBS were conducted, followed by rinsing with PBS several times, thereby achieving equilibration with PBS.

According to this, a laminate having three layers superposed therein in a state where the collagen vitrigel membrane containing an FITC-labeled goat anti-mouse IgG antibody was interposed between two sheets of the collagen vitrigel membranes could be fabricated. This laminate contained 15.0 mg of collagen and reflected the shape of the inner circle with a diameter of 34 mm of the wall surface mold.

The thus fabricated laminate of collagen vitrigel membranes (derived from the 0.25% collagen sol of (2.0 mL+2.0 mL+2.0 mL (6 mL in total)) was measured for the thickness according to the method of Example 6. As a result, the thickness was 60±3 μm (average value after the measurement of three times).

In addition, this laminate of collagen vitrigel membranes was transferred into a hydrophobic polystyrene-made culture Petri dish of 100 mm×100 mm, in which Parafilm was laid on the bottom surface thereof, and allowed to stand for complete drying within the collagen gel for about one day within a clean bench under a condition at 10.0° C. and at a humidity of 40% in a state where a lid thereof was removed. Thereafter, the Petri dish was covered with a lid and sterilely stored and maintained at room temperature to allow the vitrification to proceed, thereby fabricating a laminate of superposed dried collagen vitrigel membranes, in which the dried collagen vitrigel containing an FITC-labeled goat anti-mouse IgG antibody was interposed between two sheets of the dried collagen vitrigel membranes. The laminate of dried collagen vitrigel membranes fabricated in this step contained 1.65 mg of collagen per unit area (1.0 $cm^2$).

Figure 11A:
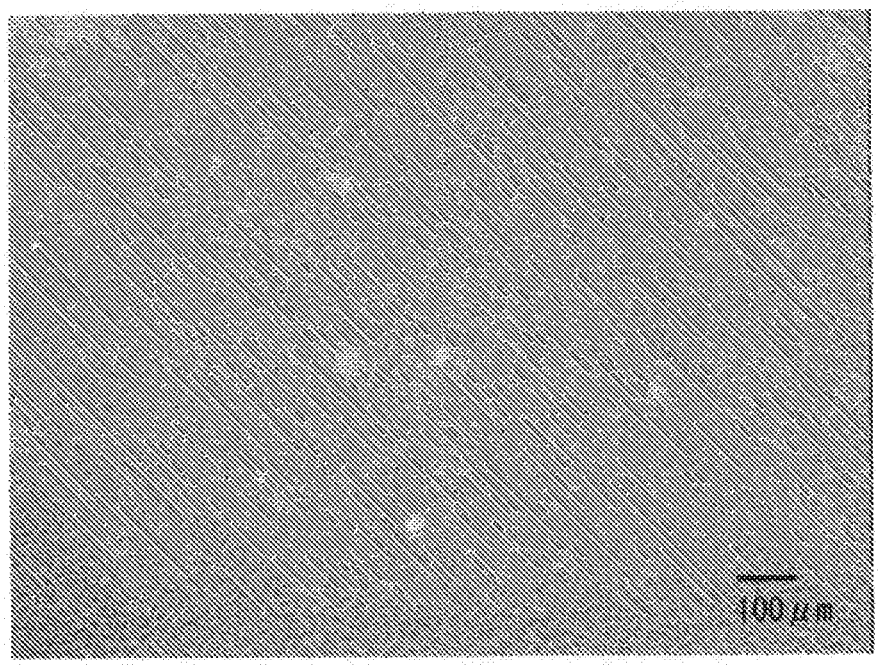
FIG. 11(A) is a view resulting from observation of a laminate of dried vitrigel membrane containing an FITC-labeled goat anti-mouse antibody fabricated in Example 8, which was rehydrated with PBS, by using a fluorescence microscope (Nikon)
Figure 11B:
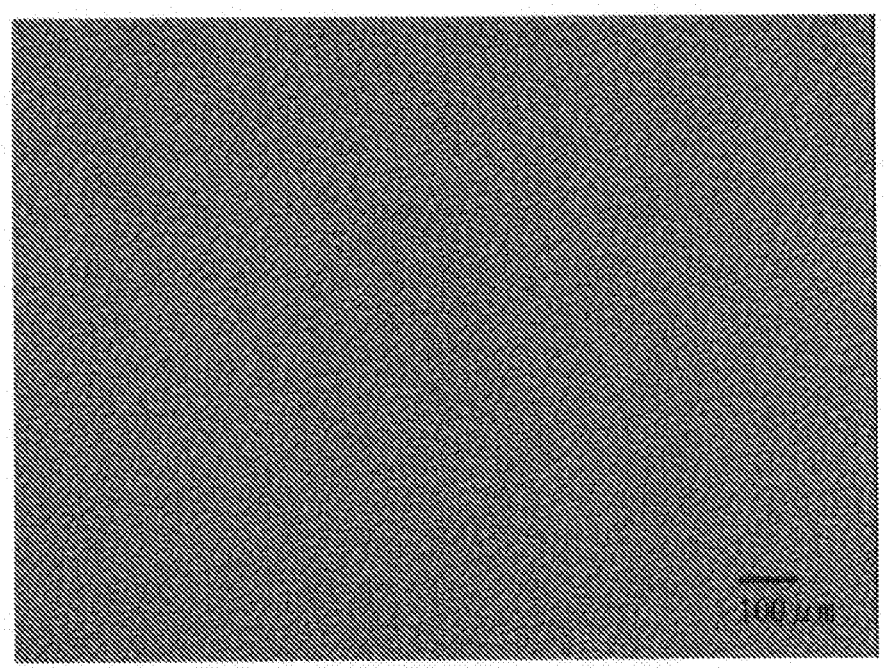
FIG. 11(B) is a view resulting from observation of a laminate fabricated by a method of Example 6.

In addition, this laminate of dried collagen vitrigel membranes was rehydrated with PBS and observed with a fluorescence microscope (Nikon). As a result, fluorescence (green color) inherent to FITC could be observed (FIG. 11(A)). Incidentally, in the laminate fabricated by the method of Example 6, the fluorescence inherent to FITC could not be observed (FIG. 11(B), magnification: 10 times).

Figure 12:
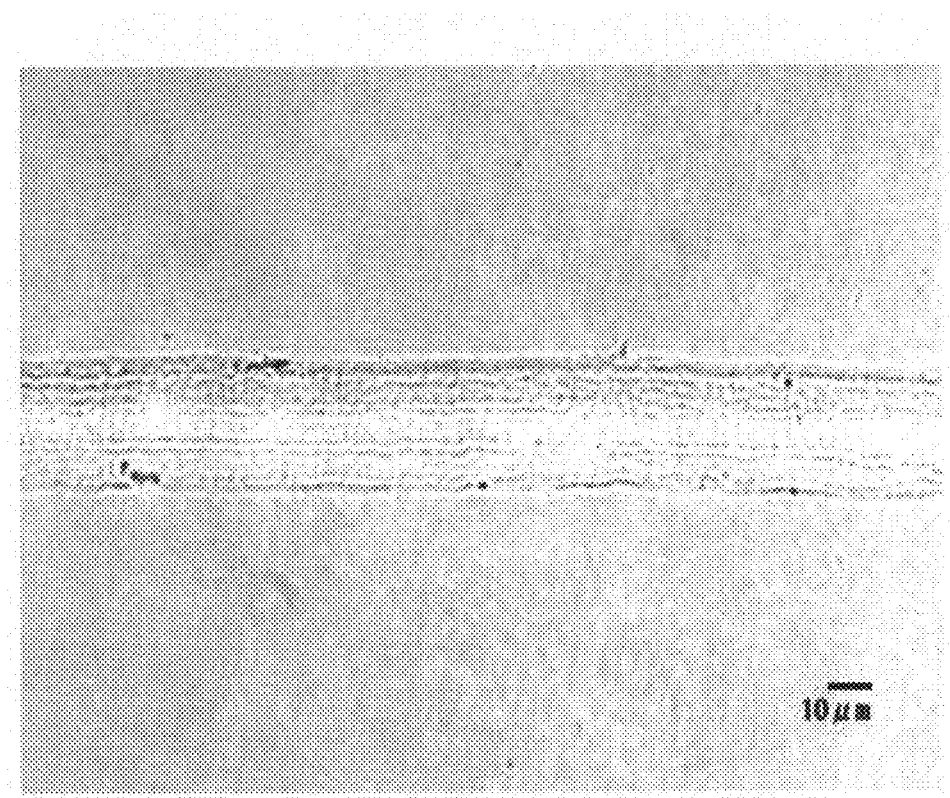
FIG. 12 is a vertical cross-sectional view of a vitrigel membrane showing the localization of an FITC-labeled goat anti-mouse antibody in a vitrigel membrane fabricated in Example 8.

Then, with respect to the fabricated laminate of collagen vitrigel membranes, how the FITC-labeled goat anti-mouse antibody was located in the vitrigel membrane was observed. Specifically, this laminate of collagen vitrigel membranes was imbedded in a Tissue-Tek O.C.T. compound and frozen. The frozen sample was sliced in a thickness of 5 μm within a cryostat. As a result, the fluorescence inherent to FITC remained in the interlayer of the collagen vitrigel membrane having a three-layer structure and could be observed (FIG. 12, magnification: 40 times).

Furthermore, it was confirmed that the FITC-labeled goat anti-mouse antibody was gradually released from the fabricated laminate of dried collagen vitrigel membranes. Specifically, the laminate of dried collagen vitrigel membranes was put in a container, and 5 mL of PBS was injected, followed by keeping in a moisturized incubator at 37.0° C. At the day 3, PBS was recovered, and 5 mL of PBS was newly injected, followed by keeping in the same manner. At the day 6, PBS was again recovered, and each PBS was measured by a fluorescent plate reader (Molecular Devices). As a result, the FITC-labeled goat anti-mouse antibody was detected in an amount of 5.53±0.21% (average value after the measurement of three times) at the day 3 and 1.62±0.08% (average value after the measurement of three times) at the day 6, respectively in PBS (in the case where the amount of the FITC-labeled goat anti-mouse antibody used for the fabrication was defined as 100%). Incidentally, in the fabrication step of the laminate of dried collagen vitrigel membranes (in PBS of the rehydration), 8.33% of the FITC-labeled goat anti-mouse antibody was detected. It became clear from the foregoing that the FITC-labeled goat anti-mouse antibody remaining in the interlayer in the fabricated laminate of dried collagen vitrigel membranes was gradually released into PBS via the outer layer of the laminate.

Example 9

Fabrication of Dried Collagen Vitrigel Membrane Having Agarose Vitrigel Membrane in Interlayer A bottom surface of a hydrophobic polystyrene-made culture Petri dish of 100 mm×100 mm was used as a substrate, and four acrylic resin-made molds with a diameter of an outer circle of 38 mm, a diameter of an inner circle of 34 mm, and a height of 30 mm were used as a wall surface mold. Four wall surface molds were placed on one substrate, thereby fabricating four containers capable of separating the substrate and the wall surface mold from each other. One sheet of a ring-shaped nylon membrane support was inserted into each of the containers, 2.0 mL of a 0.25% collagen sol was injected, and the substrate was covered with a lid of the Petri dish, followed by gelation within a moisturized incubator at 37.0° C. in the presence of 5.0% of $CO_2$ and 95% of air, thereby fabricating four collagen gels on one substrate.

At the two-hour period after transferring into the moisturized incubator at 37.0° C., the wall surface mold was slightly moved in the vertical direction, thereby unfastened the adhesion between the collagen gel and the wall surface mold. Thereafter, free water was discharged to the outside of the wall surface mold in a proportion of about ⅓ at the four- to six-hour period, and therefore, the wall surface mold was removed from the substrate. After removing the discharged free water, the collagen gel was transferred into a clean bench under a condition at 10.0° C. and at a humidity of 40%. Thereafter, the free water remaining within the collagen gel was completely removed by means of natural drying for 2 days in a state where the lid of the Petri dish was removed, thereby obtaining a dried collagen gel.

This vitrified dried collagen gel was rehydrated by the addition of 10 mL of a cell culture medium (having the same composition as that in Example 1) within the Petri dish of the substrate and released from the substrate, thereby fabricating four ring-shaped nylon membrane support-provided collagen vitrigel membranes.

Furthermore, one wall surface mold was placed on a substrate (hydrophobic polystyrene Petri dish with a diameter of 60 mm), thereby fabricating one container capable of separating the substrate and the wall surface mold from each other. One sheet of the ring-shaped nylon membrane support-provided collagen vitrigel membrane was inserted into this container.

Then, 2.0 mL of 2% agarose containing a 1% FITC-labeled goat anti-mouse IgG antibody was injected into this container. The 2% agarose containing a 1% FITC-labeled goat anti-mouse IgG antibody was prepared by cooling 2% agarose prepared by adding 0.2 g of agarose (Nippon Gene) to 9.9 mL of PBS and heating for dissolution, to about 37° C., further adding 0.1 mL of an FITC-labeled goat anti-mouse IgG antibody solution, and well mixing the contents.

After gelation at room temperature, a series of operations of complete removal of free water under a condition at 10.0° C. and a humidity of 40% and rehydration with 10 mL of a cell culture medium were conducted, thereby fabricating a laminate in which the collagen vitrigel membrane and the agarose gel membrane containing an FITC-labeled goat anti-mouse IgG antibody were superposed (ring-shaped nylon membrane support-provided collagen-agarose vitrigel membrane).

Furthermore, after removing the cell culture medium, one wall surface mold was placed on one substrate, thereby again fabricating a container capable of separating the substrate and the wall surface mold from each other. One sheet of this laminate (ring-shaped nylon membrane support-provided collagen-agarose vitrigel membrane) was inserted into this container.

Similar to the foregoing manners, 2.0 mL of a 0.25% collagen sol was injected into each of the containers, and a series of operations including gelation, discharge of free water within the collagen gel, complete removal of free water under a condition at 10.0° C. and at a humidity of 40%, and rehydration with 20 mL of PBS were conducted, thereby fabricating a laminate of three layers of vitrigel membranes superposed therein, in which the agarose vitrigel membrane containing an FITC-labeled goat anti-mouse IgG antibody was interposed between two sheets of the collagen vitrigel membranes (ring-shaped nylon membrane support-provided collagen-agarose vitrigel membrane). Then, this laminate was rinsed with PBS several times, thereby fabricating one laminate of vitrigel membranes equilibrated with PBS. This laminate of vitrigel membranes contained 10.0 mg of collagen and 40.0 mg of agarose and reflected the shape of the inner circle with a diameter of 34 mm of the wall surface mold.

In addition, the thus fabricated laminate of collagen vitrigel membranes (derived from 2.0 mL of the 0.25% collagen sol+2.0 mL of the 2% agarose sol+2.0 mL of the 0.25% collagen sol (6 mL in total)) was measured for the thickness according to the method of Example 6. As a result, the thickness was 556±13 µm (average value after the measurement of three times).

Furthermore, this laminate was transferred into a hydrophobic polystyrene-made culture Petri dish of 100 mm×100 mm, in which Parafilm was laid on the bottom surface thereof, and allowed to stand for complete drying within the collagen gel for about one day within a clean bench under a condition at 10.0° C. and at a humidity of 40% in a state where a lid thereof was removed. Thereafter, the Petri dish was covered with a lid and sterilely stored and maintained at room temperature to allow the vitrification to proceed, thereby fabricating a laminate having three layers superposed therein, in which the dried agarose vitrigel membrane containing an FITC-labeled goat anti-mouse IgG antibody was interposed between two sheets of the dried collagen vitrigel membranes (ring-shaped nylon membrane support-provided dried collagen-agarose vitrigel membrane).

The laminate of dried vitrigel membranes fabricated in this step contained 1.1 mg of collagen and 4.4 mg of agarose per unit area (1.0 cm$^2$).

Figure 13:
FIG. 13 is a view resulting from observation of a laminate of dried vitrigel membrane containing agarose fabricated in Example 9, which was rehydrated with PBS, by using a fluorescence microscope.

Furthermore, the fabricated laminate of dried vitrigel membranes was rehydrated with PBS and observed with a fluorescence microscope (Nikon). As a result, fluorescence (green color) inherent to FITC could be observed (FIG. 13, magnification: 10 times).

Example 10

Study on Improvement of Transparency of Thin Vitrigel Membrane

In view of the fact that in Example 4, the vitrigel membrane having a thicker thickness than that in the prior art could be fabricated, in order to increase the practicality, an improvement of the transparency as one of characteristics of the vitrigel membrane was studied.

Ten sheets of dried vitrigel membranes (derived from 2 mL of the 0.25% collagen sol) having a long vitrification period (3 months or more) fabricated according to the method of Example 1 were prepared, and each of them was rehydrated with 3 mL of PBS. After the rehydration, the vitrigel membranes were superposed one by one such that air was not incorporated therein.

Figure 14:
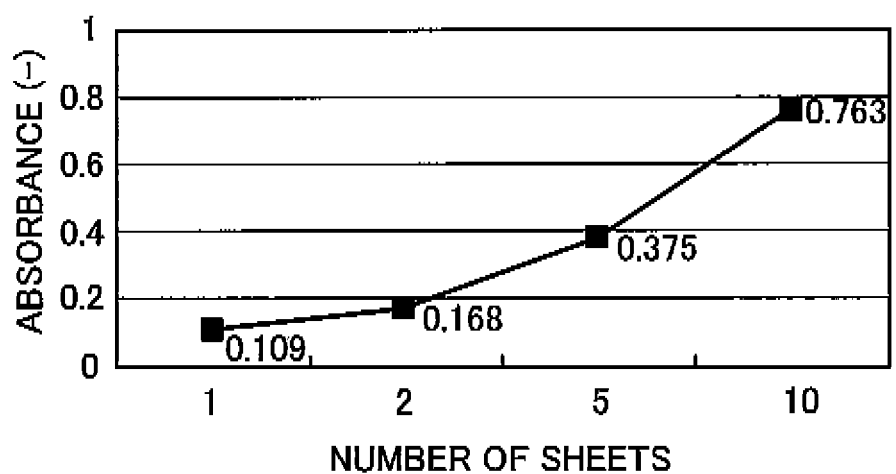
FIG. 14 is a view showing a change in absorbance with respect to a non-integrated laminate in the case of increasing the number of sheets of vitrigel membranes to be superposed.

In the course of superposition, the transparency of the vitrigel membrane was measured using a spectrophotometer (JASCO) in terms of absorbance (measuring wavelength: 400 nm). As a result, the absorbance of each case was 0.148 at the time of one sheet, 0.208 at the time of two sheets, 0.415 at the time of five sheets, and 0.803 at the time of ten sheets, respectively (FIG. 14).

In addition, at that time, the thick collagen vitrigel membrane (derived from 20 ml of the 0.25% collagen sol) having a long vitrification period (3 months or more) fabricated according to the method of Example 4 was rehydrated with PBS and similarly measured for the absorbance. As a result, the absorbance was 1.67.

Figure 15:
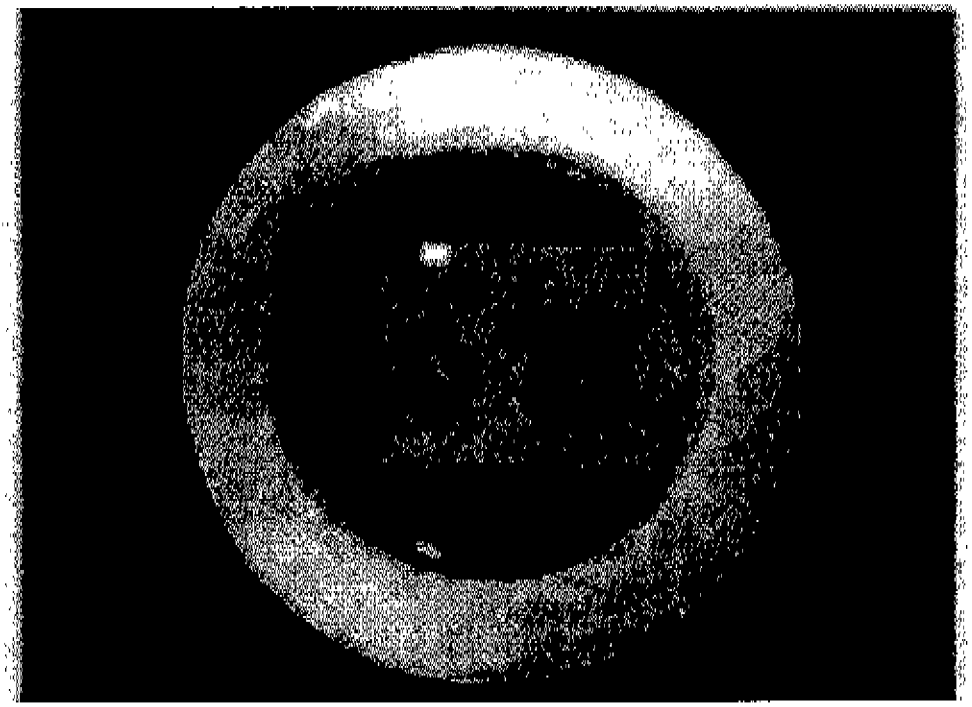
FIG. 15 is a view showing the transparency with respect to a non-integrated laminate where ten sheets of vitrigel membranes are superposed.

The more the sheet number of the vitrigel membranes to be superposed was, the more the absorbance was, and the lower the transparency was. However, the absorbance at the time of superposing ten sheets of vitrigel membranes was ½ of the absorbance of one sheet of the thick dried vitrigel membrane (derived from 20 mL of the 0.25% collagen sol), and the former was more transparent. By superposing non-integrated vitrigel membranes in which the vitrification was advanced, the transparency at the time of rehydration could be improved (FIG. 15). Accordingly, by superposing plural sheets of vitrigel membranes to make a desired thickness, the resultant can be utilized as an equivalent of collagen constituting mainly a substance of a cornea, which is excellent in the transparency.

Example 11

Fabrication of Thick Vitrigel Membrane with Excellent Transparency

A bottom surface of a hydrophobic polystyrene-made culture Petri dish of 100 mm×100 mm was used as a substrate, and an acrylic resin-made container with a diameter of an outer circle of 38 mm, a diameter of an inner circle of 34 mm, and a height of 18 mm was used as a wall surface mold. After injecting 1.0 mL of a 0.25% collagen sol into the container, nine sheets of dried vitrigel membranes (derived from 2 mL of the 0.25% collagen sol) having a long vitrification period (3 months or more) fabricated according to Example 1 were inserted. After the insertion, 1.0 mL of a 0.25% collagen sol was injected, and the substrate was covered with a lid of the Petri dish, followed by gelation for 2 hours within a moisturized incubator at 37.0° C. in the presence of 5.0% of $CO_2$ and 95% of air.

Two hours after the gelation, the wall surface mold was slightly moved in the vertical direction, thereby unfastened the adhesion between the collagen sol and the wall surface mold. Free water was discharged to the outside of the wall surface mold in a proportion of about ½ at the two-hour period, and therefore, the wall surface mold was removed from the substrate. After removing the discharged free water, the collagen gel was transferred into a clean bench under a condition at 10.0° C. and at a humidity of 40%, and the free water remaining within the collagen sol was completely removed for 2 days in a state where the lid of the Petri dish was removed. After removing the free water, 10 mL of PBS was charged in the Petri dish, and rinsing was conducted several times. After rinsing, the collagen gel was again transferred into a clean bench under a condition at 10.0° C. and at a humidity of 40%, and the free water remaining within the collagen sol was removed in a state where the lid of the Petri dish was removed, thereby obtaining a laminate of dried collagen vitrigel membranes integrated by means of superposition.

The transparency of a vitrigel membrane obtained by rehydrating this laminate of dried vitrigel membranes (inserted with nine sheets; derived from 1.0 mL of the 0.25% collagen sol+nine layers of 2.0 mL of the 0.25% collagen sol+1.0 mL of the 0.25% collagen sol) was measured using a spectrophotometer (JASCO) in terms of absorbance (measuring wavelength: 400 nm). As a result, the absorbance was 1.06 (average value after the measurement of three times).

In addition, at that time, the dried thick vitrigel membrane (derived from 20 mL of the 0.25% collagen sol) fabricated according to the method of Example 4 was rehydrated with PBS and similarly measured for the absorbance. As a result, the absorbance was 2.12 (average value after the measurement of three times).

Figure 16:
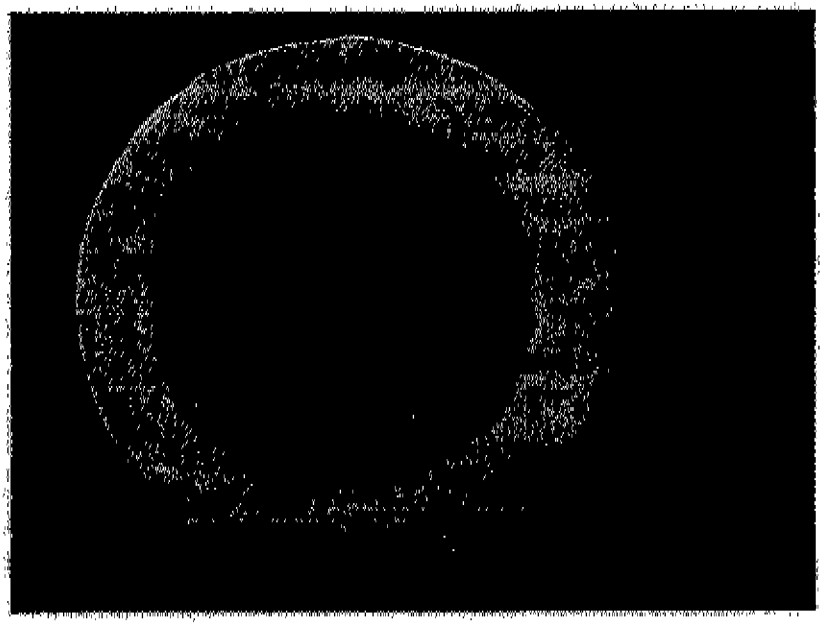
FIG. 16 is a view showing the transparency of a laminate integrated by inserting nine sheets of vitrigel membranes (derived from 1.0 mL of 0.25 collagen sol+(2.0 mL of 0.25% collagen sol)×nine layers+1.0 mL of 0.25 collagen sol).

It was noted from the foregoing that the fabrication method by integration by superposition is improved in terms of the transparency of a thick vitrigel membrane as compared with a single fabrication method (FIG. 16). Accordingly, by superposing plural sheets of vitrigel membranes and integrating them to make a desired thickness, the resultant can be utilized as an equivalent of collagen constituting mainly a substance of a cornea, which is excellent in the transparency.

The invention claimed is:

1. A method for producing a dried vitrigel membrane having a desired shape, comprising the following steps of:
    placing a wall surface mold, which is a cylindrical frame body not having a top surface and a bottom surface and having a shape the same as the desired shape, onto a substrate such that a gap is formed between a surface of the substrate and an underside of the cylindrical frame of the wall surface mold;
    adding a hydrosol to the inside of the wall surface mold;
    forming a hydrogel by gelation of the hydrosol in the inside of the wall surface mold;
    allowing a part of a free water within the hydrogel to discharge horizontally through the gap between the surface of the substrate and the underside of the cylindrical frame of the wall surface mold while maintaining the hydrogel in the inside of the wall surface mold;
    removing the wall surface mold from the top of the substrate;
    drying the hydrogel to remove residual free water, thereby fabricating a vitrified dried hydrogel;
    rehydrating the dried hydrogel to fabricate a vitrigel membrane; and
    redrying the vitrigel membrane to remove free water, thereby fabricating a vitrified dried vitrigel membrane, which does not have an amorphous outer peripheral edge.

2. The method for producing a dried vitrigel membrane according to claim 1, wherein in the adding step, a support is introduced into the hydrosol in the inside of the wall surface mold.

3. The method for producing a dried vitrigel membrane according to claim 1, wherein in the allowing step, an amount of the free water within the hydrogel is reduced to from about ¼ to ¾.

4. The method for producing a dried vitrigel membrane according to claim 1, wherein in the redrying step, the dried vitrigel membrane is vitrified on a film possessing a capacity facilitating the detachability of the dried vitrigel membrane.

5. The method for producing a dried vitrigel membrane according to claim 4, wherein the film is Parafilm.

* * * * *